US006156546A

United States Patent [19]
Konkel et al.

[11] Patent Number: 6,156,546
[45] Date of Patent: Dec. 5, 2000

[54] IDENTIFICATION AND MOLECULAR CLONING OF A GENE ENCODING A FIBRONECTIN BINDING PROTEIN (CADF) FROM CAMPYLOBACTER COLI AND CAMPYLOBACTER JEJUNI

[75] Inventors: Michael E. Konkel; Steven G. Garvis, both of Pullman, Wash.

[73] Assignee: Washington State University Research Foundation, Pullman, Wash.

[21] Appl. No.: 09/080,025

[22] Filed: May 15, 1998

Related U.S. Application Data

[60] Provisional application No. 60/046,763, May 16, 1997.
[51] Int. Cl.[7] .............................. C12P 19/34; C12Q 1/68; C07H 21/04
[52] U.S. Cl. ........................... 435/91.2; 435/6; 536/23.1; 536/24.3; 536/24.31; 536/24.32; 536/24.33
[58] Field of Search ................................ 536/23.1, 24.33, 536/24.31, 24.32, 24.3; 435/91.2, 6

[56] References Cited

U.S. PATENT DOCUMENTS

| | | | |
|---|---|---|---|
| 4,816,397 | 3/1989 | Boss et al. | 435/68 |
| 5,470,958 | 11/1995 | Blaser et al. | 424/164.1 |

OTHER PUBLICATIONS

Garvis et al. Abstracts of the 97th general meeting of american society for Mirobiology. May 4–8, 1997. p. 106.
Oyofo et al. Journal of clinical microbiology. 30(10). p. 2613–2619, Oct. 1992.
Stonnet et al. FEMS Immunology and Medical Microbiology. 7 p. 337–334, 1993.
Stonnet et al. Eur. J. Clin. Microbiol. Dis. 14. 355–359, 1995.
Taylor et al. Molecular and cellular probes. 4, 261–271, 1990.
Baloda, S. B. et al., *FEMS Micrbiol. Lett.* 28:1–5 (1985).
Bellido, F. et al., *J. Bacteriol.* 174:5196–5203 (1992).
Bolla, J.–M. et al., *J. Bacteriol.* 177:4266–4271 (1995).
Chen, R. et al., *Eur. J. Biochem.* 163:73–77 (1987).
Dawson, J. R. et al., *Infect. Immun.* 58:3924–3928 (1990).
De Melo, M. A. et al., *Infect. Immun.* 58:1749–1756 (1990).
De Mot, R. et al., *Mol. Gen. Genet.* 231:489–493 (1992).
De Mot, R. et al., *Microbiol.* 140:1377–1387 (1994).
De Mot, R. et al., *FEMS Microbiol. Lett.* 81:323–328 (1991).
Deich, R. A. et al., *J. Bacteriol.* 170:489–498 (1988).
Engleberg, N. C. et al., *Mol. Microbiol.* 5:2021–2029 (1991).
Fauchere, J. L. et al., *Infect. Immun.* 4:283–287 (1986).
Frohman G. et al., *Proc. Natl. Acad. Sci. USA* 85:8998–9002 (1988).
Froman, G. et al., *J. Biol. Chem.* 259:14899–14905 (1984).
Garvis, S. G. et al., *Infect Immun.* 64:3537–3543 (1996).
Huse, W. D. et al., *Science* 246:1275–1281 (1989).
Isberg, R. R. et al., *Annu. Rev. Genet.* 28:395–422 (1994).
Keski–Oja, J. et al., *Rev. Infect. Dis.* 9:S404–S411 (1987).
Koebnik, R., *Mol. Microbiol.* 16:1269–1270 (1995).
Konkel, M. E. et al., *Infect. Immun.* 60:4945–4949 (1992).
Konkel, M. E. et al., *J. Med. Microbiol.* 37:30–37 (1992).
Konkel, M. E. et al., *Infect. Immun.* 57:2984–2990 (1989).
Konkel, M. E. et al., *Infect. Immun.* 64:1850–1853 (1996).
Konkel, M. E. et al., *J. Infect. Dis.* 168:948–954 (1993b).
Konkel, M. E. et al., *Mol. Microbiol.* 24:953–963 (1997).
Kuusela, P., *Nature (Lond)* 276:718–720 (1978).
Kuusela, P. et al., *Biochem. Biophys. Acta.* 993:297–300 (1989).
Lazzaroni, J.–C. et al., *Mol. Microbiol.* 6:735–742 (1992).
Loh, E. Y. et al., *Science* 243:217–222 (1989).
Logan, S. M. et al., *Infect. Immun.* 38:898–906 (1982).
Ludwig, B. et al., *Infect. Immun.* 59:2515–21 (1991).
McSweegan, E. et al., *Infect. Immun.* 53:141–148 (1986).
Moser, I. et al., *Med. Microbiol. Immunol.* 184:147–153 (1995).
Myhre, E. B. et al., *Infect. Immun.* 40:29–34 (1983).
Nelson, M. B. et al., *Infect. Immun.* 56:128–134 (1988).
Nikaido, H. et al., *J. Biol. Chem.* 266:770–779 (1991).
Pei, Z. et al., *J. Biol. Chem.* 268:18717–18725 (1993).
Pei, Z. et al., *J. Biol. Chem.* 266:16363–16369 (1991).
Quaroni, A. et al., *Proc. Natl. Acad. Sci. USA* 75:5548–5552(1978).
Thomas, D. D. et al., *J. Exp. Med.* 161:514–525 (1985).
Tibor, A. et al., *Infect. Immun.* 62:3633–3639 (1994).
von Heijne, G., *J. Mol. Biol.* 184:99–105 (1985).
Wyler, D. J., *Rev. Infect. Dis.* 9:S391–S399 (1987).

*Primary Examiner*—Jeffrey Fredman
*Assistant Examiner*—Juliet C. Einsmann
*Attorney, Agent, or Firm*—Christensen O'Connor Johnson & Kindness PLLC

[57] ABSTRACT

A novel gene encoding a 37 kDa outer membrane protein from *Campylobacter coli* M275 has been cloned and sequenced. This protein has been named CadF and is expressed in a large number of clinical isolates of Campylobacter species. The invention also provides assays for detecting the presence of pathogenic Campylobacter species based on the antibody-based detection of CadF, or the polymerase chain reaction (PCR)-based amplification of a segment of the *C. coli* cadF gene.

14 Claims, No Drawings

SEQUENCE LISTING

<160> NUMBER OF SEQ ID NOS: 19

<210> SEQ ID NO 1
<211> LENGTH: 981
<212> TYPE: DNA
<213> ORGANISM: Campylobacter coli
<220> FEATURE:
<221> NAME/KEY: CDS
<222> LOCATION: (1)..(978)

<400> SEQUENCE: 1

| | | | | | | | | | | | | | | | | |
|---|---|---|---|---|---|---|---|---|---|---|---|---|---|---|---|---|
| atg | aaa | aag | tta | tta | cta | tgt | tta | ggg | ttg | tca | agc | gtt | tta | ttt | ggt | 48 |
| Met | Lys | Lys | Leu | Leu | Leu | Cys | Leu | Gly | Leu | Ser | Ser | Val | Leu | Phe | Gly | |
| 1 | | | | 5 | | | | | 10 | | | | | 15 | | |
| gca | gat | aac | aat | gta | aaa | ttt | gaa | atc | act | cct | act | ttg | aat | cac | aat | 96 |
| Ala | Asp | Asn | Asn | Val | Lys | Phe | Glu | Ile | Thr | Pro | Thr | Leu | Asn | His | Asn | |
| | | | 20 | | | | | 25 | | | | | 30 | | | |
| tat | ttt | gaa | ggt | aat | tta | gat | atg | gat | aat | cgc | tat | gca | cca | ggg | att | 144 |
| Tyr | Phe | Glu | Gly | Asn | Leu | Asp | Met | Asp | Asn | Arg | Tyr | Ala | Pro | Gly | Ile | |
| | | 35 | | | | | 40 | | | | | 45 | | | | |
| aga | cta | ggg | tat | cat | ttt | gat | gat | ttt | tgg | ctt | gat | caa | tta | gaa | cta | 192 |
| Arg | Leu | Gly | Tyr | His | Phe | Asp | Asp | Phe | Trp | Leu | Asp | Gln | Leu | Glu | Leu | |
| | 50 | | | | | 55 | | | | | 60 | | | | | |
| ggt | tta | gaa | cat | tac | tcg | gat | gta | aaa | tat | aca | aat | tct | act | ctt | acc | 240 |
| Gly | Leu | Glu | His | Tyr | Ser | Asp | Val | Lys | Tyr | Thr | Asn | Ser | Thr | Leu | Thr | |
| 65 | | | | | 70 | | | | | 75 | | | | | 80 | |
| acc | gat | att | act | aga | act | tat | ttg | agt | gct | att | aaa | ggc | att | gat | tta | 288 |
| Thr | Asp | Ile | Thr | Arg | Thr | Tyr | Leu | Ser | Ala | Ile | Lys | Gly | Ile | Asp | Leu | |
| | | | | 85 | | | | | 90 | | | | | 95 | | |
| ggt | gag | aaa | ttt | tat | ttt | tat | ggt | tta | gct | ggt | ggg | gga | tat | gag | gat | 336 |
| Gly | Glu | Lys | Phe | Tyr | Phe | Tyr | Gly | Leu | Ala | Gly | Gly | Gly | Tyr | Glu | Asp | |
| | | | 100 | | | | | 105 | | | | | 110 | | | |
| ttt | tct | aaa | ggc | gct | ttt | gat | aat | aaa | agt | gga | gga | ttt | ggc | cat | tat | 384 |
| Phe | Ser | Lys | Gly | Ala | Phe | Asp | Asn | Lys | Ser | Gly | Gly | Phe | Gly | His | Tyr | |
| | | 115 | | | | | 120 | | | | | 125 | | | | |
| gga | gca | ggt | tta | aaa | ttt | cgc | ctt | agt | gat | tct | tta | gct | tta | aga | ctt | 432 |
| Gly | Ala | Gly | Leu | Lys | Phe | Arg | Leu | Ser | Asp | Ser | Leu | Ala | Leu | Arg | Leu | |
| | 130 | | | | | 135 | | | | | 140 | | | | | |
| gaa | aca | aga | gat | caa | att | tct | ttc | cat | gat | gca | gat | cat | agt | tgg | gtt | 480 |
| Glu | Thr | Arg | Asp | Gln | Ile | Ser | Phe | His | Asp | Ala | Asp | His | Ser | Trp | Val | |
| 145 | | | | | 150 | | | | | 155 | | | | | 160 | |
| tca | act | ttg | ggt | att | agt | ttt | ggc | ttt | ggc | gct | aag | aga | gaa | aaa | gtt | 528 |
| Ser | Thr | Leu | Gly | Ile | Ser | Phe | Gly | Phe | Gly | Ala | Lys | Arg | Glu | Lys | Val | |
| | | | | 165 | | | | | 170 | | | | | 175 | | |
| gta | gcc | gaa | caa | gta | aaa | gaa | gta | gct | ata | gaa | cct | cgt | gta | gct | gta | 576 |
| Val | Ala | Glu | Gln | Val | Lys | Glu | Val | Ala | Ile | Glu | Pro | Arg | Val | Ala | Val | |
| | | | 180 | | | | | 185 | | | | | 190 | | | |
| cct | aca | caa | tca | caa | tgt | cct | gca | gag | cca | aga | gag | ggt | gct | atg | cta | 624 |
| Pro | Thr | Gln | Ser | Gln | Cys | Pro | Ala | Glu | Pro | Arg | Glu | Gly | Ala | Met | Leu | |
| | | 195 | | | | | 200 | | | | | 205 | | | | |
| gat | gaa | aat | ggt | tgt | gaa | aaa | aca | att | tct | ttt | gaa | gga | cat | ttt | ggt | 672 |
| Asp | Glu | Asn | Gly | Cys | Glu | Lys | Thr | Ile | Ser | Phe | Glu | Gly | His | Phe | Gly | |
| | 210 | | | | | 215 | | | | | 220 | | | | | |

```
ttt gat aag gta gat atc aat cca gcc ttt gaa gaa aaa atc aaa gaa       720
Phe Asp Lys Val Asp Ile Asn Pro Ala Phe Glu Glu Lys Ile Lys Glu
225                 230                 235                 240 att gct caa ctt tta gat gaa aat gca aga tat gat act att tta gag       768
Ile Ala Gln Leu Leu Asp Glu Asn Ala Arg Tyr Asp Thr Ile Leu Glu
            245                 250                 255 ggt cat act gat aat ata ggc tca aga gca tac aat caa aaa ctt tca       816
Gly His Thr Asp Asn Ile Gly Ser Arg Ala Tyr Asn Gln Lys Leu Ser
        260                 265                 270 gaa aga cgg gct gaa agc gtt gca aaa gaa ctt gaa aaa ttt ggt gta       864
Glu Arg Arg Ala Glu Ser Val Ala Lys Glu Leu Glu Lys Phe Gly Val
    275                 280                 285 gat aaa gat cgt atc cag aca gtt ggt tat ggt caa gat aaa cct cgc       912
Asp Lys Asp Arg Ile Gln Thr Val Gly Tyr Gly Gln Asp Lys Pro Arg
290                 295                 300 tca aga aat gag acc aaa gag ggt aga gca gat aac aga aga gtg gat       960
Ser Arg Asn Glu Thr Lys Glu Gly Arg Ala Asp Asn Arg Arg Val Asp
305                 310                 315                 320 gct aaa ttt atc cta aga taa                                           981
Ala Lys Phe Ile Leu Arg
                325

<210> SEQ ID NO 2
<211> LENGTH: 326
<212> TYPE: PRT
<213> ORGANISM: Campylobacter coli

<400> SEQUENCE: 2

Met Lys Lys Leu Leu Cys Leu Gly Leu Ser Ser Val Leu Phe Gly
 1               5                  10                  15

Ala Asp Asn Asn Val Lys Phe Glu Ile Thr Pro Thr Leu Asn His Asn
                20                  25                  30

Tyr Phe Glu Gly Asn Leu Asp Met Asp Asn Arg Tyr Ala Pro Gly Ile
            35                  40                  45

Arg Leu Gly Tyr His Phe Asp Asp Phe Trp Leu Asp Gln Leu Glu Leu
        50                  55                  60

Gly Leu Glu His Tyr Ser Asp Val Lys Tyr Thr Asn Ser Thr Leu Thr
65                  70                  75                  80

Thr Asp Ile Thr Arg Thr Tyr Leu Ser Ala Ile Lys Gly Ile Asp Leu
                85                  90                  95

Gly Glu Lys Phe Tyr Phe Tyr Gly Leu Ala Gly Gly Tyr Glu Asp
            100                 105                 110

Phe Ser Lys Gly Ala Phe Asp Asn Lys Ser Gly Gly Phe Gly His Tyr
        115                 120                 125

Gly Ala Gly Leu Lys Phe Arg Leu Ser Asp Ser Leu Ala Leu Arg Leu
    130                 135                 140

Glu Thr Arg Asp Gln Ile Ser Phe His Asp Ala Asp His Ser Trp Val
145                 150                 155                 160

Ser Thr Leu Gly Ile Ser Phe Gly Phe Gly Ala Lys Arg Glu Lys Val
                165                 170                 175

Val Ala Glu Gln Val Lys Glu Val Ala Ile Glu Pro Arg Val Ala Val
            180                 185                 190

Pro Thr Gln Ser Gln Cys Pro Ala Glu Pro Arg Glu Gly Ala Met Leu
        195                 200                 205

Asp Glu Asn Gly Cys Glu Lys Thr Ile Ser Phe Glu Gly His Phe Gly
    210                 215                 220

Phe Asp Lys Val Asp Ile Asn Pro Ala Phe Glu Glu Lys Ile Lys Glu
```

```
                    225                 230                 235                 240

Ile Ala Gln Leu Leu Asp Glu Asn Ala Arg Tyr Asp Thr Ile Leu Glu
                245                 250                 255

Gly His Thr Asp Asn Ile Gly Ser Arg Ala Tyr Asn Gln Lys Leu Ser
            260                 265                 270

Glu Arg Arg Ala Glu Ser Val Ala Lys Glu Leu Glu Lys Phe Gly Val
        275                 280                 285

Asp Lys Asp Arg Ile Gln Thr Val Gly Tyr Gly Gln Asp Lys Pro Arg
    290                 295                 300

Ser Arg Asn Glu Thr Lys Glu Gly Arg Ala Asp Asn Arg Arg Val Asp
305                 310                 315                 320

Ala Lys Phe Ile Leu Arg
                325

<210> SEQ ID NO 3
<211> LENGTH: 350
<212> TYPE: PRT
<213> ORGANISM: Pseudomonas aeruginosa

<400> SEQUENCE: 3

Met Lys Leu Lys Asn Thr Leu Gly Val Val Ile Gly Ser Leu Val Ala
  1               5                  10                  15

Ala Ser Ala Met Asn Ala Phe Ala Gln Gly Gln Asn Ser Val Glu Ile
                 20                  25                  30

Glu Ala Phe Gly Lys Arg Tyr Phe Thr Asp Ser Val Arg Asn Met Lys
             35                  40                  45

Asn Ala Asp Leu Tyr Gly Gly Ser Ile Gly Tyr Phe Leu Thr Asp Asp
         50                  55                  60

Val Glu Leu Ala Leu Ser Tyr Gly Glu Tyr His Asp Val Arg Gly Thr
 65                  70                  75                  80

Tyr Glu Thr Gly Asn Lys Lys Val His Gly Asn Leu Thr Ser Leu Asp
                 85                  90                  95

Ala Ile Tyr His Phe Gly Thr Pro Gly Val Gly Leu Arg Pro Tyr Val
            100                 105                 110

Ser Ala Gly Leu Ala His Gln Asn Ile Thr Asn Ile Asn Ser Asp Ser
        115                 120                 125

Gln Gly Arg Gln Gln Met Thr Met Ala Asn Ile Gly Ala Gly Leu Lys
    130                 135                 140

Tyr Tyr Phe Thr Glu Asn Phe Phe Ala Lys Ala Ser Leu Asp Gly Gln
145                 150                 155                 160

Tyr Gly Leu Glu Lys Arg Asp Asn Gly His Gln Gly Glu Trp Met Ala
                165                 170                 175

Gly Leu Gly Val Gly Phe Asn Phe Gly Gly Ser Lys Ala Ala Pro Ala
            180                 185                 190

Pro Glu Pro Val Ala Asp Val Cys Ser Asp Ser Asp Asn Asp Gly Val
        195                 200                 205

Cys Asp Asn Val Asp Lys Cys Pro Asp Thr Pro Ala Asn Val Thr Val
    210                 215                 220

Asp Ala Asn Gly Cys Pro Ala Val Ala Glu Val Val Arg Val Gln Leu
225                 230                 235                 240

Asp Val Lys Phe Asp Phe Asp Lys Ser Lys Val Lys Glu Asn Ser Tyr
                245                 250                 255

Ala Asp Ile Lys Asn Leu Ala Asp Phe Met Lys Gln Tyr Pro Ser Thr
            260                 265                 270
```

```
Ser Thr Thr Val Glu Gly His Thr Asp Ser Val Gly Thr Asp Ala Tyr
            275                 280                 285

Asn Gln Lys Leu Ser Glu Arg Arg Ala Asn Ala Val Arg Asp Val Leu
        290                 295                 300

Val Asn Glu Tyr Gly Val Gly Gly Arg Val Asn Ala Val Gly Tyr
305                 310                 315                 320

Gly Glu Ser Arg Pro Val Ala Asp Asn Ala Thr Ala Glu Gly Arg Ala
                325                 330                 335

Ile Asn Arg Arg Val Glu Ala Glu Val Glu Ala Glu Ala Lys
                340                 345                 350

<210> SEQ ID NO 4
<211> LENGTH: 326
<212> TYPE: PRT
<213> ORGANISM: Pseudomonas fluorescens

<400> SEQUENCE: 4

Met Lys Leu Lys Asn Thr Leu Gly Phe Ala Ile Gly Ser Ile Ile Ala
 1                5                  10                  15

Ala Thr Ser Phe Gly Ala Leu Ala Gln Gly Gln Gly Ala Val Glu Gly
                20                  25                  30

Glu Leu Phe Tyr Lys Lys Gln Tyr Asn Asp Ser Val Lys His Ile Glu
            35                  40                  45

Asp Gly Phe Asn Pro Gly Ala Arg Ile Gly Tyr Phe Leu Thr Asp Asp
        50                  55                  60

Leu Ser Leu Asn Leu Ser Tyr Asp Lys Thr Asn His Thr Arg Ser Asn
65                  70                  75                  80

Asp Gly Thr Gly Ser Gln Lys Ile Gly Gly Asp Thr Ser Ser Leu Thr
                85                  90                  95

Ala Gln Tyr His Phe Gly Gln Ala Gly Val Asp Ser Leu Arg Pro Tyr
            100                 105                 110

Val Glu Gly Gly Phe Gly His Gln Ser Arg Gly Asn Val Lys Ala Asp
        115                 120                 125

Gly His Ser Gly Arg Asp Gln Ser Thr Leu Ala Ile Ala Gly Ala Gly
130                 135                 140

Val Lys Tyr Tyr Phe Thr Asn Asn Val Tyr Ala Arg Ala Gly Val Glu
145                 150                 155                 160

Ala Asp Tyr Ala Leu Asp Asn Gly Lys Trp Asp Tyr Ser Ala Leu Val
                165                 170                 175

Gly Leu Gly Val Asn Phe Gly Gly Asn Ala Gly Ala Ala Ala Pro Ala
            180                 185                 190

Pro Thr Pro Ala Pro Ala Pro Glu Pro Thr Pro Glu Pro Glu Ala Pro
        195                 200                 205

Val Ala Gln Val Val Arg Val Glu Leu Asp Val Lys Phe Asp Phe Asp
210                 215                 220

Lys Ser Val Val Lys Pro Asn Ser Tyr Gly Asp Val Lys Asn Leu Ala
225                 230                 235                 240

Asp Phe Met Ala Gln Tyr Pro Ala Thr Asn Val Glu Val Ala Gly His
                245                 250                 255

Thr Asp Ser Ile Gly Pro Asp Ala Tyr Asn Gln Lys Leu Ser Gln Arg
            260                 265                 270

Arg Ala Asp Arg Val Lys Gln Val Leu Val Lys Asp Gly Val Ala Pro
        275                 280                 285

Ser Arg Ile Thr Ala Val Gly Tyr Gly Glu Ser Arg Pro Val Ala Asp
290                 295                 300
```

```
Asn Ala Thr Glu Ala Gly Arg Ala Val Asn Arg Val Glu Ala Ser
305                 310                 315                 320

Val Glu Ala Gln Ala Gln
            325

<210> SEQ ID NO 5
<211> LENGTH: 861
<212> TYPE: DNA
<213> ORGANISM: Campylobacter jejuni
<220> FEATURE:
<221> NAME/KEY: CDS
<222> LOCATION: (1)..(861)

<400> SEQUENCE: 5 gca agt gtt tta ttt ggt gct gat aac aat gta aaa ttt gaa atc act    48
Ala Ser Val Leu Phe Gly Ala Asp Asn Asn Val Lys Phe Glu Ile Thr
 1               5                  10                  15 cca act tta aac tat aat tac ttt gaa ggt aat tta gat atg gat aat    96
Pro Thr Leu Asn Tyr Asn Tyr Phe Glu Gly Asn Leu Asp Met Asp Asn
                20                  25                  30 cgt tat gca cca ggt gtt aga ctt ggt tat cat ttt gac gat ttt tgg   144
Arg Tyr Ala Pro Gly Val Arg Leu Gly Tyr His Phe Asp Asp Phe Trp
             35                  40                  45 ctt gat caa tta gaa ttt ggg tta gag cat tat tct gat gtt aaa tat   192
Leu Asp Gln Leu Glu Phe Gly Leu Glu His Tyr Ser Asp Val Lys Tyr
     50                  55                  60 aca aat aca aat aaa act aca gat att aca aga act tat ttg agt gct   240
Thr Asn Thr Asn Lys Thr Thr Asp Ile Thr Arg Thr Tyr Leu Ser Ala
 65                  70                  75                  80 att aaa ggt att gat gta ggt gag aaa ttt tat ttc tat ggt tta gca   288
Ile Lys Gly Ile Asp Val Gly Glu Lys Phe Tyr Phe Tyr Gly Leu Ala
                 85                  90                  95 ggt gga gga tat gag gat ttt tca aat gct gct tat gat aat aaa agc   336
Gly Gly Gly Tyr Glu Asp Phe Ser Asn Ala Ala Tyr Asp Asn Lys Ser
            100                 105                 110 ggt gga ttt gga cat tat ggc acg ggt gta aaa ttc tgt ctt agt gat   384
Gly Gly Phe Gly His Tyr Gly Thr Gly Val Lys Phe Cys Leu Ser Asp
        115                 120                 125 tct ttg gct tta aga ctt gaa act aga gat caa att aat ttt aat cat   432
Ser Leu Ala Leu Arg Leu Glu Thr Arg Asp Gln Ile Asn Phe Asn His
130                 135                 140 gca aac cat aat tgg gtt tca act tta ggt att agt ttt ggt ttt ggt   480
Ala Asn His Asn Trp Val Ser Thr Leu Gly Ile Ser Phe Gly Phe Gly
145                 150                 155                 160 ggc aaa aag gaa aaa gct gta gaa gaa gtt gct gat act cgt cca gct   528
Gly Lys Lys Glu Lys Ala Val Glu Glu Val Ala Asp Thr Arg Pro Ala
                165                 170                 175 cca caa gca aaa tgt cct gtt gaa cca aga gaa ggt gct ttg tta gat   576
Pro Gln Ala Lys Cys Pro Val Glu Pro Arg Glu Gly Ala Leu Leu Asp
            180                 185                 190 gaa aat ggt tgc gaa aaa act att tct ttg gaa ggt cat ttt ggt ttt   624
Glu Asn Gly Cys Glu Lys Thr Ile Ser Leu Glu Gly His Phe Gly Phe
        195                 200                 205 gat aaa act act ata aat cca act ttt caa gaa aaa atc aaa gaa att   672
Asp Lys Thr Thr Ile Asn Pro Thr Phe Gln Glu Lys Ile Lys Glu Ile
    210                 215                 220 gca aaa gtt tta gat gaa aat gaa aga tat gat act att ctt gaa gga   720
Ala Lys Val Leu Asp Glu Asn Glu Arg Tyr Asp Thr Ile Leu Glu Gly
225                 230                 235                 240 cat aca gat aat att ggt tca aga gct tat aat caa aag ctt tct gaa   768
```

-continued

```
His Thr Asp Asn Ile Gly Ser Arg Ala Tyr Asn Gln Lys Leu Ser Glu
                245                 250                 255 aga cgt gct aaa agt gtt gct aat gaa ctt gaa aaa tat ggt gta gaa        816
Arg Arg Ala Lys Ser Val Ala Asn Glu Leu Glu Lys Tyr Gly Val Glu
        260                 265                 270 aaa agt cgc atc aaa aca gta ggt tat ggt caa gat aat cct cgc            861
Lys Ser Arg Ile Lys Thr Val Gly Tyr Gly Gln Asp Asn Pro Arg
            275                 280                 285
```

<210> SEQ ID NO 6
<211> LENGTH: 287
<212> TYPE: PRT
<213> ORGANISM: Campylobacter jejuni

<400> SEQUENCE: 6

```
Ala Ser Val Leu Phe Gly Ala Asp Asn Asn Val Lys Phe Glu Ile Thr
 1               5                  10                  15

Pro Thr Leu Asn Tyr Asn Tyr Phe Glu Gly Asn Leu Asp Met Asp Asn
            20                  25                  30

Arg Tyr Ala Pro Gly Val Arg Leu Gly Tyr His Phe Asp Asp Phe Trp
        35                  40                  45

Leu Asp Gln Leu Glu Phe Gly Leu Glu His Tyr Ser Asp Val Lys Tyr
    50                  55                  60

Thr Asn Thr Asn Lys Thr Thr Asp Ile Thr Arg Thr Tyr Leu Ser Ala
65                  70                  75                  80

Ile Lys Gly Ile Asp Val Gly Glu Lys Phe Tyr Phe Tyr Gly Leu Ala
                85                  90                  95

Gly Gly Gly Tyr Glu Asp Phe Ser Asn Ala Ala Tyr Asp Asn Lys Ser
            100                 105                 110

Gly Gly Phe Gly His Tyr Gly Thr Gly Val Lys Phe Cys Leu Ser Asp
        115                 120                 125

Ser Leu Ala Leu Arg Leu Glu Thr Arg Asp Gln Ile Asn Phe Asn His
    130                 135                 140

Ala Asn His Asn Trp Val Ser Thr Leu Gly Ile Ser Phe Gly Phe Gly
145                 150                 155                 160

Gly Lys Lys Glu Lys Ala Val Glu Glu Val Ala Asp Thr Arg Pro Ala
                165                 170                 175

Pro Gln Ala Lys Cys Pro Val Glu Pro Arg Glu Gly Ala Leu Leu Asp
            180                 185                 190

Glu Asn Gly Cys Glu Lys Thr Ile Ser Leu Glu Gly His Phe Gly Phe
        195                 200                 205

Asp Lys Thr Thr Ile Asn Pro Thr Phe Gln Gly Lys Ile Lys Glu Ile
    210                 215                 220

Ala Lys Val Leu Asp Glu Asn Glu Arg Tyr Asp Thr Ile Leu Glu Gly
225                 230                 235                 240

His Thr Asp Asn Ile Gly Ser Arg Ala Tyr Asn Gln Lys Leu Ser Glu
                245                 250                 255

Arg Arg Ala Lys Ser Val Ala Asn Glu Leu Glu Lys Tyr Gly Val Glu
            260                 265                 270

Lys Ser Arg Ile Lys Thr Val Gly Tyr Gly Gln Asp Asn Pro Arg
        275                 280                 285
```

<210> SEQ ID NO 7
<211> LENGTH: 861
<212> TYPE: DNA
<213> ORGANISM: Campylobacter jejuni
<220> FEATURE:

<221> NAME/KEY: CDS
<222> LOCATION: (1)..(861)

<400> SEQUENCE: 7

```
gca agt gtt tta ttt ggt cgt gat aac aat gta aaa ttt gaa atc act         48
Ala Ser Val Leu Phe Gly Arg Asp Asn Asn Val Lys Phe Glu Ile Thr
 1               5                  10                  15 cca act tta aac tat aat tac ttt gaa ggt aat tta gat atg gat aat         96
Pro Thr Leu Asn Tyr Asn Tyr Phe Glu Gly Asn Leu Asp Met Asp Asn
             20                  25                  30 cgt tat gca cca ggg att aga ctt ggt tat cat ttt gac gat ttt tgg        144
Arg Tyr Ala Pro Gly Ile Arg Leu Gly Tyr His Phe Asp Asp Phe Trp
         35                  40                  45 ctt gat caa tta gaa ttt ggg tta gag cat tat tct gat gtt aaa tat        192
Leu Asp Gln Leu Glu Phe Gly Leu Glu His Tyr Ser Asp Val Lys Tyr
     50                  55                  60 aca aat act aat aaa act aca gat att aca aga act tat ttg agt gct        240
Thr Asn Thr Asn Lys Thr Thr Asp Ile Thr Arg Thr Tyr Leu Ser Ala
 65                  70                  75                  80 att aaa ggt att gat gta ggt gag aaa ttt tat ttc tat ggt tta gca        288
Ile Lys Gly Ile Asp Val Gly Glu Lys Phe Tyr Phe Tyr Gly Leu Ala
                 85                  90                  95 ggt gga gga tat gag gat ttt tca aat gct gct tat gat aat aaa agc        336
Gly Gly Gly Tyr Glu Asp Phe Ser Asn Ala Ala Tyr Asp Asn Lys Ser
            100                 105                 110 ggt gga ttt gga cat tat ggc gcg ggt gta aaa ttc cgt ctt agt gat        384
Gly Gly Phe Gly His Tyr Gly Ala Gly Val Lys Phe Arg Leu Ser Asp
        115                 120                 125 tct ttg gct tta aga ctt gaa act aga gat caa att aat ttt aat cat        432
Ser Leu Ala Leu Arg Leu Glu Thr Arg Asp Gln Ile Asn Phe Asn His
    130                 135                 140 gca aac cat aat tgg gtt tca act tta ggt att agt ttt ggt ttt ggt        480
Ala Asn His Asn Trp Val Ser Thr Leu Gly Ile Ser Phe Gly Phe Gly
145                 150                 155                 160 ggc aaa aag gaa aaa gct gta gaa gaa gtt gct gat act cgt cca gct        528
Gly Lys Lys Glu Lys Ala Val Glu Glu Val Ala Asp Thr Arg Pro Ala
                165                 170                 175 cca caa gca aaa tgt cct gtt cct tca aga gaa ggt gct ttg tta gat        576
Pro Gln Ala Lys Cys Pro Val Pro Ser Arg Glu Gly Ala Leu Leu Asp
            180                 185                 190 gaa aat ggt tgc gaa aaa act att tct ttg gaa ggt cat ttt ggt ttt        624
Glu Asn Gly Cys Glu Lys Thr Ile Ser Leu Glu Gly His Phe Gly Phe
        195                 200                 205 gat aaa act act ata aat cca act ttt caa gaa aaa atc aaa gaa att        672
Asp Lys Thr Thr Ile Asn Pro Thr Phe Gln Glu Lys Ile Lys Glu Ile
    210                 215                 220 gca aaa gtt tta gat gaa aat gaa aga tat gat act att ctt gaa gga        720
Ala Lys Val Leu Asp Glu Asn Glu Arg Tyr Asp Thr Ile Leu Glu Gly
225                 230                 235                 240 cat aca gat aat atc ggt tca aga gct tat aat caa aag ctt tct gaa        768
His Thr Asp Asn Ile Gly Ser Arg Ala Tyr Asn Gln Lys Leu Ser Glu
                245                 250                 255 aga cgt gct aaa agt gtt gct aat gaa ctt gaa aaa tat ggt gta gaa        816
Arg Arg Ala Lys Ser Val Ala Asn Glu Leu Glu Lys Tyr Gly Val Glu
            260                 265                 270 aaa agt cgc atc aaa aca gta ggt tat ggt caa gat aat cct cgc            861
Lys Ser Arg Ile Lys Thr Val Gly Tyr Gly Gln Asp Asn Pro Arg
        275                 280                 285
```

<210> SEQ ID NO 8

<211> LENGTH: 287
<212> TYPE: PRT
<213> ORGANISM: Campylobacter jejuni

<400> SEQUENCE: 8

```
Ala Ser Val Leu Phe Gly Arg Asp Asn Asn Val Lys Phe Glu Ile Thr
 1               5                  10                  15

Pro Thr Leu Asn Tyr Asn Tyr Phe Glu Gly Asn Leu Asp Met Asp Asn
             20                  25                  30

Arg Tyr Ala Pro Gly Ile Arg Leu Gly Tyr His Phe Asp Asp Phe Trp
         35                  40                  45

Leu Asp Gln Leu Glu Phe Gly Leu Glu His Tyr Ser Asp Val Lys Tyr
     50                  55                  60

Thr Asn Thr Asn Lys Thr Thr Asp Ile Thr Arg Thr Tyr Leu Ser Ala
 65                  70                  75                  80

Ile Lys Gly Ile Asp Val Gly Glu Lys Phe Tyr Phe Tyr Gly Leu Ala
                 85                  90                  95

Gly Gly Gly Tyr Glu Asp Phe Ser Asn Ala Ala Tyr Asp Asn Lys Ser
            100                 105                 110

Gly Gly Phe Gly His Tyr Gly Ala Gly Val Lys Phe Arg Leu Ser Asp
        115                 120                 125

Ser Leu Ala Leu Arg Leu Glu Thr Arg Asp Gln Ile Asn Phe Asn His
    130                 135                 140

Ala Asn His Asn Trp Val Ser Thr Leu Gly Ile Ser Phe Gly Phe Gly
145                 150                 155                 160

Gly Lys Lys Glu Lys Ala Val Glu Val Ala Asp Thr Arg Pro Ala
                165                 170                 175

Pro Gln Ala Lys Cys Pro Val Pro Ser Arg Glu Gly Ala Leu Leu Asp
            180                 185                 190

Glu Asn Gly Cys Glu Lys Thr Ile Ser Leu Glu Gly His Phe Gly Phe
        195                 200                 205

Asp Lys Thr Thr Ile Asn Pro Thr Phe Gln Glu Lys Ile Lys Glu Ile
    210                 215                 220

Ala Lys Val Leu Asp Glu Asn Glu Arg Tyr Asp Thr Ile Leu Glu Gly
225                 230                 235                 240

His Thr Asp Asn Ile Gly Ser Arg Ala Tyr Asn Gln Lys Leu Ser Glu
                245                 250                 255

Arg Arg Ala Lys Ser Val Ala Asn Glu Leu Glu Lys Tyr Gly Val Glu
            260                 265                 270

Lys Ser Arg Ile Lys Thr Val Gly Tyr Gly Gln Asp Asn Pro Arg
        275                 280                 285
```

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: PCR primer CadF-F38
<220> FEATURE:
<221> NAME/KEY: misc_binding
<222> LOCATION: (1)..(26)
<223> OTHER INFORMATION: PCR primer homologous to the 5' end of the cadF-M275 gene.

<400> SEQUENCE: 9
atgaaaaagt tattactatg tttacg        26

```
<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: PCR
      primer CadF-R20
<220> FEATURE:
<221> NAME/KEY: misc_binding
<222> LOCATION: (1)..(18)
<223> OTHER INFORMATION: PCR primer homologous to the 3' end of the
      cadF-M275 gene

<400> SEQUENCE: 10
aggataaatt tagcatcc                                                 18

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: PCR
      primer CadF-F2B
<220> FEATURE:
<221> NAME/KEY: misc_binding
<222> LOCATION: (1)..(20)
<223> OTHER INFORMATION: PCR primer (forward) useful for amplifying
      cadF genes from C. coli or C. jejuni

<400> SEQUENCE: 11
ttgaaggtaa tttagatatg                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:  PCR
      primer CadF-R1B
<220> FEATURE:
<221> NAME/KEY: misc_binding
<222> LOCATION: (1)..(20)
<223> OTHER INFORMATION: PCR primer (reverse) useful for amplifing
      cadF genes from C. coli or C. jejuni

<400> SEQUENCE: 12
ctaataccta aagttgaaac                                               20

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:  PCR
      primer CadF-F38
<220> FEATURE:
<221> NAME/KEY: misc_binding
<222> LOCATION: (1)..(26)
<223> OTHER INFORMATION: PCR primer (forward) useful for amplifing
      cadF genes from C. coli and C. jejuni

<400> SEQUENCE: 13 atgaaaagt tattactatg tttagg                                         26

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:  PCR
      primer CadF-R20
```

```
<220> FEATURE:
<221> NAME/KEY: misc_binding
<222> LOCATION: (1)..(18)
<223> OTHER INFORMATION: PCR primer (reverse) useful for amplifing
      cadF genes from C. coli and C. jejuni

<400> SEQUENCE: 14
aggataaatt tagcatcc                                                 18

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:  PCR
      primer
<220> FEATURE:
<221> NAME/KEY: misc_binding
<222> LOCATION: (1)..(20)
<223> OTHER INFORMATION: PCR primer (forward) useful for amplifing
      cadF genes from C. coli and C. jejuni

<400> SEQUENCE: 15
ttgaaggtaa tttagatatg                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:  PCR
      primer CadF-R1C
<220> FEATURE:
<221> NAME/KEY: misc_binding
<222> LOCATION: (1)..(20)
<223> OTHER INFORMATION: PCR primer (reverse) useful for amplification
      of cadF genes from C. coli and C. jejuni

<400> SEQUENCE: 16
cttcttttac ttgttcggct                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:  PCR
      primer
<220> FEATURE:
<221> NAME/KEY: misc_binding
<222> LOCATION: (1)..(20)
<223> OTHER INFORMATION: PCR primer (forward) useful for amplification
      of cadF genes from C. coli and C. jejuni

<400> SEQUENCE: 17
ttgaaggtaa tttagatatg                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:  PCR
      primer CadF-R1E
<220> FEATURE:
<221> NAME/KEY: misc_binding
<222> LOCATION: (1)..(20)
<223> OTHER INFORMATION: PCR primer (reverse) useful for amplification
      of cadF genes from C. coli and C. jejuni

<400> SEQUENCE: 18
```

-continued

```
cattgtgatt gtgtaggtac                                              20

<210> SEQ ID NO 19
<211> LENGTH: 14
<212> TYPE: PRT
<213> ORGANISM: Campylobacter coli
<220> FEATURE:
<221> NAME/KEY: UNSURE
<222> LOCATION: (12)
<223> OTHER INFORMATION: N-terminal sequence was uncertain at amino
      acid residue 12

<400> SEQUENCE: 19

Ala Asp Asn Asn Val Lys Phe Glu Ile Thr Pro Xaa Leu Asn
 1               5                  10
```

IDENTIFICATION AND MOLECULAR CLONING OF A GENE ENCODING A FIBRONECTIN BINDING PROTEIN (CADF) FROM CAMPYLOBACTER COLI AND CAMPYLOBACTER JEJUNI

RELATED APPLICATIONS

This application claims the benefit of priority of U.S. Provisional Application No. 60/046,763 filed May 16, 1997, under 35 U.S.C. §119.

FIELD OF THE INVENTION

Gene encoding an outer membrane protein found in *Campylobacter coli* and *Campylobacter jejuni* isolates and methods for detecting virulent Campylobacter spp.

BACKGROUND OF THE INVENTION

This work was supported in part by a grant from the National Institute of Health of the United States government (1R01 DK50567-01A1). The government has certain rights in the invention.

Campylobacter species, primarily *C. jejuni* and *C. coli*, are recognized as a major cause of gastrointestinal disease (Skirrow and Blaser, 1992), with between 2 to 8 million cases of campylobacteriosis, and an estimated 200 to 800 deaths per year in the United States. Infection with *C. jejuni* or *C. coli* is characterized by the sudden onset of fever, abdominal cramps, and diarrhea with blood and leukocytes. These two species of Campylobacter are very closely related. Though they can be differentiated by a biochemical test, clinically they are associated with virtually the same symptoms, and generally are treated with the same antibiotics. In addition to acute gastrointestinal disease, infection with *C. jejuni* has been shown to be a frequent antecedent to the development of Guillain-Barre-type polyneuropathy (Kuroki et al., 1991; Yuki et al., 1993). Despite the prevalence and complications associated with Campylobacter infections worldwide, relatively few rapid tests are available for the detection of these organisms.

The binding of many pathogenic bacteria to cells is an important virulence determinant as it prevents the colonizing bacteria from being swept away by mechanical cleansing forces such as peristalsis and fluid flow, and thus permits the subsequent internalization of the bacteria into "non-professional phagocytic cells," i.e., cells that can phagocytize only particles that adhere via a receptor-ligand interaction. As in the case of other intestinal pathogens, the ability of *C. coli* and *C. jejuni* to colonize the gastrointestinal tract by binding to epithelial or other cells has been proposed to be essential for their ability to cause disease. Fauchere et al. (Fauchere et al., 1986) found that *C. jejuni* isolated from individuals with fever and diarrhea exhibited greater binding to epithelial cells than strains isolated from individuals without diarrhea or fever. Studies have been performed to identify and characterize potential Campylobacter adhesins that mediate the organism's attachment to host cells. Possible adhesins include outer membrane proteins (omps) and lipopolysaccharide (McSweegan and Walker, 1986). Others (De Melo and Pechere, 1990) have identified four proteins with apparent molecular masses of 28, 32, 36, and 42 kDa that bind to HEp-2 cells. A *C. jejuni* gene encoding a 28 kDa protein, termed PEB1, has been identified and has been proposed to be an adhesin (Pei et al., 1991; Blaser et al., U.S. Pat. No. 5,470,958; Pei and Blaser, 1993). PEB1 shares homology with periplasmic binding proteins involved in nutrient acquisition (Garvis et al., 1996). However, the specific roles of these various proteins in binding and their respective ligands on *C. jejuni* or *C. coli* binding to host cells remain unclear.

Many pathogenic microorganisms are capable of binding to components of the extracellular matrix (ECM), such as fibronectin (Fn), laminin, vitronectin, and collagen and may use such interactions during the initial phases of infection. Protozoan parasites such as Leishmania and *Trypanosoma cruzi* (Wyler, 1987), viral pathogens including hepatitis A and influenza A (Keski-Oja et al., 1987), and bacterial pathogens including *Treponema denticola* (Dawson and Ellen, 1990; Thomas et al., 1986), *Streptococcus pyogenes* (Myhre and Kuusela, 1983), *Staphlococcus aureus* (Kuusela, 1978), *Salmonella enteriditis* (Baloda et al., 1985), and enterotoxigenic *Escherichia coli* (Froman et al., 1984) have all been shown to bind to Fn. More recently, *C. jejuni* has been also reported to bind to Fn and other ECM components (Kuusela et al., 1989; Moser and Schroder, 1995).

There are many possible sources of infection with *C. jejuni* and *C. coli*, as they are part of the normal intestinal flora in a wide range of birds and mammals. Large scale outbreaks of human campylobacteriosis have been reported which are usually linked to the consumption of polluted water and raw milk. Pets, especially cats, also can carry these organisms. Sporadic cases of campylobacteriosis are more common and are associated with the consumption of undercooked chicken. As few as 500 Campylobacter organisms are believed to be capable of causing disease. In the United States, case-control studies have attributed 48–70% of the sporadic infections with the consumption of Campylobacter-contaminated chickens. A recent report, using 1,000 fresh chickens bought at grocery stores in 36 cities, revealed that 63% of the chickens tested harbored Campylobacter spp. (Consumer Reports 63:12–18, 1998). This finding is not surprising given the potential for chickens to be heavily cross-contaminated during mechanized processing. Hence, methods for the rapid detection of Campylobacter spp. in foods and for their diagnosis in patients are needed.

SUMMARY OF THE INVENTION

The present invention provides a newly identified and characterized adhesion protein from *C. coli* and *C. jejuni*. This polymorphic protein was identified initially in *C. coil* M275 (formerly *C. jejuni* M275) by virtue of its ability to specifically bind fibronectin. Binding assays using immobilized extracellular matrix proteins and soluble fibronectin showed that *C. coli* showed specific and saturable binding to fibronectin. Ligand immunoblot assays using $^{125}$I-labeled fibronectin (Fn) revealed that the labeled protein bound specifically with an outer membrane protein of *C. coli* having an apparent molecular mass of 37 kDa. Moreover, biotinylated fibronectin was shown to bind to a protein with an apparent molecular mass of 37 kDa in extracts of outer membrane proteins from wild-type *C. jejuni*. This new protein has been designated "CadF" for Campylobacter adhesion to Fn, and has been shown to mediate the specific binding of *C. coli* and *C. jejuni* to fibronectin.

A rabbit antiserum, raised against the gel-purified protein, reacted with a 37 kDa protein in several *C. jejuni* and *C. coli* isolates (n=46) as judged by immunoblot analysis, thus indicating that CadF is conserved among these two Campylobacter species. Antibodies present in convalescent serum from *C. jejuni*-infected individuals also recognized a 37 kDa protein. Mutant strains of *C. jejuni* that lacked CadF were shown to exhibit reduced binding to fibronectin and showed a reduced level of binding to cultured epithelial cells, thus confirming that CadF is involved in adhesion, which is a prerequisite for virulence.

Three representative examples of a cadF gene encoding this immunoreactive 37 kDa protein were cloned and sequenced. One of these cadF genes, cadF-M275, was sequenced in its entirety and was found to contain an open reading frame that encodes a protein of 326 amino acids with a calculated molecular mass of 36,872 Daltons, which includes a 16 residue signal peptide at the $NH_2$-terminus.

The isolated CadF protein and the cloned cadF gene were used to develop rapid detection assays for *C. jejuni* and *C. coli* based either on the polymerase chain reaction (PCR), or based on the use of antibodies against CadF. In one such PCR-based assay, primers based on the cadF nucleotide sequence were used to amplify an internal DNA fragment of approximately 400 bp. The specificity of this PCR test was demonstrated by showing that these primers amplified the 400 bp fragment from thirty-eight of forty (95%) *C. jejuni* isolates and five of six (83.3%) *C. coli* isolates. An antiserum against CadF was also used to detect methanol-fixed *C. jejuni* and *C. coli* organisms using an indirect immunofluorescence microscopy assay. As neither of these assays requires the bacteria to be cultured, both are useful for the rapid detection of pathogenic *C. jejuni* and *C. coli* in food products or in stool samples of infected-individuals. In addition, antibodies reactive against CadF protein were detected in convalescent serum from several *C. jejuni*-infected individuals (n=5).

DETAILED DESCRIPTION OF THE PREFERRED EMBODIMENT

In view of the prevalence of Campylobacter contamination, there is a need for vaccines to protect against infection with these organisms, as well as rapid assays for the detection of Campylobacter species in food products and for the diagnosis of *Campylobacter jejuni* and *Campylobacter coli* in individuals suffering from gastrointestinal disease. To help provide such vaccines and assays, the subject invention provides isolated nucleic acid molecules that encode an outer membrane protein common to most or all strains of the pathogens *Campylobacter jejuni* and *Campylobacter coli*. This protein has been termed "CadF."

Provided here are representative nucleic acids that encode *C. jejuni* and *C. coli* CadF polypeptides as well as methods for obtaining additional *C. jejuni* and *C. coli* cadF nucleic acid molecules. By "CadF polypeptides," it is understood that such polypeptides include full-length CadF proteins, as well as subportions thereof, including peptides that may be useful for blocking adhesion or for raising antibodies. One means of identifying cadF genes from new isolates of *C. jejuni* or *C. coli* is to use cadF nucleic acids, as hybridization probes. Such probes can be prepared from an entire cadF gene or a subportion thereof, or from RNA transcripts corresponding to all or a portion of a cadF gene.

Detection of a cadF gene by hybridization depends on the formation of complementary duplexes between a probe and a target nucleic acid. The complementary duplexes that form between a probe and a target nucleic acid during hybridization may be perfectly matched, or may accommodate some mismatched (i.e., non-complementary) bases, depending on the conditions of the hybridization reactions (e.g., Sambrook et al., *Molecular Cloning: A Laboratory Manual, Second Edition*, Cold Spring Harbor, N.Y., 1989, which is incorporated herein by reference). Probes greater in length than about 50 nucleotides may accommodate up to 25–30% mismatched bases. Smaller probes will accommodate fewer mismatches. The tendency of a target and probe to form duplexes containing mismatched base pairs is controlled by the "stringency" of the hybridization conditions, which itself is a function of factors such as the concentration of salt or formamide in the hybridization buffer, the temperature of the hybridization, and the post-hybridization wash conditions. For the present purposes, it is understood that under conditions of "high stringency," the only duplexes that stably form will be perfectly complementary, or will contain no more than about 1–5% mismatched bases. Duplexes formed under conditions of moderate stringency will include perfectly matched hybrids as well as duplexes that may contain up to 20–22% mismatched bases, while duplexes formed under conditions of low stringency may contain even higher percentages of mismatches.

By applying well-known principles that govern the formation of hybrid duplexes, conditions having the desired stringency can be achieved by one skilled in the art by selecting from among a variety of hybridization buffers, temperatures, and wash conditions. Thus, conditions can be selected that permit the detection of either perfectly-matched or partially mismatched hybrid duplexes. The "Tm," or "melting temperature" of a duplex, is useful for selecting appropriate hybridization conditions. Stringent hybridization conditions for polynucleotide molecules >200 nucleotides in length typically involve hybridizing at a temperature 15°–25° C. below the melting temperature (Tm) of the expected duplex. For oligonucleotide probes (>30 nucleotides) which form less stable duplexes than longer probes, stringent hybridization usually is achieved by hybridizing at 5°–10° C. below the Tm (e.g., Sambrook et al., 1989; see Section 11.45).

The Tm of a nucleic acid duplex can be calculated using a formula based on the % G+C contained in the nucleic acids, and that takes chain length into account, such as the formula Tm=81.5–16.6 (log $[Na^+]$)+0.41 (% G+C)–(600/N), where N=chain length (Sambrook et al., 1989; see Section 11.46). This formula is especially useful for calculating the Tm of probes ranging between 14 and 70 nucleotides in length. For oligonucleotides shorter than 18 residues, the Tm can be estimated my multiplying the number of A+T residues in the duplex by 2° C., and the number of G+C residues by 4° C., and adding the two numbers together, though this method may lead to an overestimate of the Tm for longer oligonucleotides. In practice, an estimated Tm for an oligonucleotide probe is often confirmed empirically. Thus, one skilled in the art can calculate the Tm for any chosen probe whose nucleotide sequence is known or whose base composition can be estimated, and thereafter devise conditions to achieve high, moderate, or low stringency hybridization conditions as needed.

Generally, a nucleic acid probe must be at least 10, or more preferably 12, or even more preferably 15 nucleotides in length in order to form a stable hybrid. The stability of short hybrid duplexes is to some degree a function of the % G+C present in the probe. Thus, probes as short as 10 residues can form stable hybrids if they have a high G+C content, e.g., G+C>50%, especially if G and/or C residues are located near the probe termini.

In using the nucleic acid molecules of SEQ ID NO: 1, SEQ ID NO: 5 and SEQ ID NO: 7 as a source of probes for detecting new cadF genes, conditions of high or moderate stringency may be used. An example of moderately stringent conditions useful for detecting cadF genes involves hybridizing DNA bound to filters at 37° C. in a buffer containing 50% formamide and 1 M NaCl, and washing the filters after hybridization in 2×SSC at room temperature, then in 2×SSC at 37° C. to 40° C., where 1×SSC=0.15 M NaCl/0.015 M sodium citrate. However, it should be clear from the above discussion that one can manipulate the stringency of the hybridization conditions as may be required for the detection of cadF genes. Stringency can be adjusted, for example, by raising or lowering the formamide concentration and/or the hybridization temperature. Methods for hybridization and representative buffer formulations for high and low stringency hybridization are well established and are provided in the published literature (e.g., Sambrook et al., 1989; see also Hames and Higgins, eds., *Nucleic Acid Hybridization, A Practical Approach*, IRL Press, Washington D.C., 1985; Berger and Kimmel, eds., *Methods in Enzymology, Vol. 52, Guide to Molecular Cloning Techniques*, Academic Press Inc., New York, N.Y., 1987; and Bothwell, Yancopoulos and Alt, eds., *Methods for Cloning and Analysis of Eukaryotic Genes*, Jones and Bartlett Publishers, Boston, Mass. 1990; which are incorporated by reference herein in their entirety).

Although the cadF gene is found only in *C. coli* and *C. jejuni* and not in other bacteria, a comparison of three representative cadF genes (see Table 5) has indicated that this gene is highly polymorphic among individual isolates. The *C. coli* cadF gene disclosed herein, cadF-M275, differed at about 15.3% of its nucleotide residues from the two representative *C. jejuni* cadF genes. Despite their variability, cadF genes are easily distinguishable from other genes, e.g., by hybridization, because the most closely related non-Campylobacter gene (OprF, discussed above) has only 28–29% homology with cadF at the amino acid level. Because of the redundancy in the genetic code, the nucleotide sequences of oprF and cadF are expected to differ to an even greater extent than their respective product's amino acid sequences. Accordingly, one would not expect an oprF gene to cross-hybridize with a cadF probe under conditions of high or moderate stringency, and probably not even under conditions of low stringency. Thus, cadF gene variants whose nucleotide sequences may differ by 15–20% or more can be specifically detected by hybridization with cadF probes, even in the presence of other bacteria. New isolates of the cadF gene can be identified by their ability to hybridize under conditions of high or moderate stringency with nucleic acid probes corresponding to the disclosed cadF genes whose sequences are presented in SEQ ID NO: 1, SEQ ID NO: 5 and SEQ ID NO: 7.

Thus, the invention provides isolated nucleic acid molecules that encode *C. jejuni* and *C. coli* CadF polypeptides and that are capable of hybridizing under suitable conditions to a nucleic acid molecule corresponding to one of the cadF genes whose nucleotide sequences are given in SEQ ID NO: 1, SEQ ID NO: 5 and SEQ ID NO: 7 namely, cadF-M275, cadF-M129, and cadF-F38011. Moreover, DNA molecules encoding CadF proteins of interest and/or derived from the sequences of SEQ ID NO: 1, SEQ ID NO: 5 and SEQ ID NO: 7 may be prepared using generally available methods such as PCR mutagenesis, site-directed mutagenesis, and/or restriction digestion and ligation. The hybrid DNA thus obtained is then inserted into expression vectors and introduced into suitable host cells to obtain the recombinant CadF proteins.

The nucleotide sequence of a representative cadF gene, that of *C. coli* M275, is shown in SEQ ID NO: 1 and encodes the CadF polypeptide whose amino acid sequence is shown in SEQ ID NO: 2. The sequences of the *C. jejuni* M129 and F38011 cadF genes are shown in SEQ ID NO: 5 and SEQ ID NO: 7, and the CadF polypeptides encoded by these nucleic acid molecules also are encompassed by the invention [SEQ ID NOS:6 and 8, respectively.] The open reading frames for both cadF-M129 and cadF-38011 begin with the first nucleotide shown in SEQ ID NO: 5 and SEQ ID NO: 7. Thus, the first codon in these open reading frames is "GCA." The nucleotide sequences at the 5' and 3' ends of these two *C. jejuni* cadF genes have not been determined, but gel analysis of the CadF proteins expressed in C jejuni M129 and F38011 suggests that their cadF gene products are similar in size to that encoded by cadF M275. The invention thus includes three representative cadF nucleic acid molecules that encode CadF polypeptides, namely, cadF-M275, cadF-M129 and the cadF-F38011. The CadF proteins encoded by the cadF genes of this invention may contain amino acid substitutions, additions, and/or deletions as compared with the representative CadF amino acid sequences provided herein.

The CadF amino acid sequence shown in SEQ ID NO: 2 was compared with the amino acid sequences in the National Center for Biotechnology Information (NCBI) computer-searchable database. The most closely related amino acid sequences thus located corresponded to the outer membrane protein porin F (OprF) from two Pseudomonas spp., namely *P. aeruginosa*, whose OprF polypeptide had 29% identity and 53% similarity to the CadF protein, and *P. fluorescens*, whose OprF had 28% identity and 52% similarity to CadF. The longest contiguous stretch of identical amino acids found was between CadF and the Opr protein of *P. aeruginosa*. This short stretch of identity is 11 amino acids in length, and corresponds to amino acids 266–276 of the M275 CadF protein. Thus, any stretch of at least 12 contiguous amino acids of the M275 CadF protein defines a unique polypeptide that does not correspond to any previously reported polypeptide. Computerized database searches also were performed of the amino acid sequences encoded by the *C. jejuni* cadF genes of SEQ ID NO: 1, SEQ ID NO: 5 and SEQ ID NO: 7. As was found for the cadF-M275 translate, the deduced *C. jejuni* CadF proteins had the greatest homology with Pseudomonas OprF protein. Accordingly, the invention provides an isolated nucleic acid molecule that encodes a polypeptide comprising at least 12 contiguous amino acids of the amino acid sequence shown in SEQ ID NO: 2.

Based on computerized database searches showing that the CadF amino acid sequence is relatively unique, it is predicted that a cadF nucleic acid probe will not hybridize with any nucleic acid target other than one derived from another cadF gene. However, should cross-hybridization with a non-cadF gene occur based on limited regions of unexpected homology, the non-cadF nucleic acid molecule would nonetheless be distinguishable by virtue of the low signal strength that it would produce as compared with the signal strength obtained for a bona fide cadF target. Moreover, a fortuitously cross-hybridizing non-cadF isolate could be distinguished from a cadF gene by an examination of the amino acid sequence deduced from the new isolate's open reading frame. A cadF gene is expected to encode a protein having a calculated molecular mass of about 37 kDa, As shown in Table 5, translates of cadF genes will have an about 89% identity in their amino acid sequences when compared with other CadF translates. Thus, the translates of new cadF isolates are expected to contain at least 80%, or more preferably, 88–90% amino acid identity with one or more of the CadF polypeptides disclosed herein, and to encode proteins having a predicted size of about 37 kDa.

In addition, the invention further provides PCR primers useful for isolating cadF genes from many clinical isolates of C. coli and C. jejuni. A representative example of such a primer pair includes the primers CadF-F38 and CadF-R20, whose respective nucleotide sequences are 5'-ATG AAA AAG TTA TTA CTA TGT TTA GG-3' (forward) SEQ ID NO: 9 and 5'-AGG ATA AAT TTA GCA TCC-3' (reverse) SEQ ID NO: 10. CadF-F38 corresponds to the 5' end of the cadF-M275 gene, and CadF-R20, the reverse primer, to the complement of the 3' end of the cadF-M275 gene. Primer CadF-F38 corresponds to nucleic acid residues 1 through 26 of SEQ ID NO: 1 and primer CadF-R20 corresponds to the complement of nucleic acid residues 957 through 974 of SEQ ID NO: 1. The partial cadF genes of C. jejuni M129 and F3801 1, were obtained by using CadF-F38 and CadF-R20 to amplify DNA obtained from these two isolates of C. jejuni. These same primers were able to amplify the cadF gene from several additional C. jejuni isolates, though some of the isolates tested with these primers did not yield a product. Thus, cadF genes of this invention may be obtained by amplification of sequences using polymerase chain reaction (PCR) amplification (e.g., Loh et al., *Science* 243:217–222, 1989; Frohman et al., *Proc. Natl. Acad. Sci. USA* 85:8998–9002, 1988; Erlich (ed.), *PCR Technology: Principles and Applications for DNA Amplification*, Stockton Press, 1989; and Mullis et al., *PCR: The Polymerase Chain Reaction*, 1994, which are incorporated by reference herein in their entirety).

In other aspects of the invention, a DNA molecule coding a CadF protein is inserted into a suitable vector, which is in turn used to transfect or transform a suitable host cell. Suitable expression vectors for use in carrying out the present invention may include a promoter capable of directing the transcription of a polynucleotide molecule of interest in a host cell and may also include a transcription termination signal, these elements being operably linked in the vector. CadF may be expressed under the control of an inducible promoter, or may be fused to a signal peptide that directs its secretion into the culture medium. Vectors may be designed to express only a subportion of the CadF protein, e.g., to obtain peptides for use in raising antibodies against selected epitopes, or for vaccine testing. As will be evident to one skilled in the art, one can express the polypeptides of the instant invention in a wide variety of host cells such as avian, insect, and plant cells using regulatory sequences, vectors and methods well established in the literature. The invention encompasses cells transfected or transduced with the above-described recombinant expression vectors.

The present invention also provides isolated and purified CadF polypeptides, including synthetic peptides, recombinantly derived peptides, and fusion proteins. The CadF proteins according to the present invention may be purified using a number of established methods such as affinity chromatography using anti-CadF antibodies coupled to a solid support. The CadF polypeptides of the invention are encoded by cadF nucleic acid molecules such as those identified by the methods disclosed herein. A representative CadF polypeptide is shown in SEQ ID NO: 2 which depicts the CadF protein encoded by the cadF nucleic acid molecule whose nucleotide sequence is given in SEQ ID NO: 2. Further representative CadF polypeptides are those encoded by the open reading frames of cadF-M129 and cadF-F38011, which are shown in SEQ ID NO: 5 and SEQ ID NO: 7, respectively. Because the CadF protein is polymorphic among different isolates, the invention encompasses variants of the CadF polypeptide that may differ in their amino acid sequences by as much as 10%, 12%, 15%, or 20%, from the amino acid sequences of the representative CadF proteins disclosed herein. The CadF polypeptides of this invention may be obtained by the expression of isolated nucleic acid molecules derived from C. coli or C. jejuni that hybridize with probes corresponding to all or part of a cadF nucleotide sequence shown in SEQ ID NO: 1, SEQ ID NO: 5 and SEQ ID NO: 7. The subject peptides find a variety of uses, including preparation of specific antibodies.

The CadF polypeptides of the present invention provide for the construction of attenuated vaccine strains and the design of subunit-based preparations for parenteral or oral administration (Konkel et al., 1997). Thus, in one of its aspects, the invention relates to the use of CadF, and mutations, derivatives and peptide fragments thereof, in a pharmaceutical formulation for the prophylactic or therapeutic treatment of human or animal subjects. Thus, the proteins and protein fragments of the invention may be administered in combination with a pharmaceutically acceptable carrier for enhancing resistance in a mammalian host to infection by C. jejuni or C. coli.

The present invention further encompasses variants of CadF genes that, for example, are modified in a manner that results in the production of a CadF protein capable of binding to its recognition site, but unable to carry out its normal biological activity. The present invention also encompasses fragments of CadF proteins that are capable of binding the natural CadF receptor, but that are incapable of being internalized. The CadF polypeptides of the invention encompass proteins retrieved from naturally occurring materials and closely related, functionally similar proteins retrieved by antisera specific to CadF proteins, and recombinantly expressed proteins encoded by genetic materials (DNA, RNA, cDNA) retrieved on the basis of their similarity to the unique regions in the sequences disclosed herein. The invention also encompasses CadF peptides capable of preventing the adhesion of C. coli or C. jejuni to epithelial cells.

Representative uses of the nucleotide sequences and transformed host cells of the invention thus include, inter alia, the following:

1. Construction of DNA probes useful in Northern or Southern blots, dot-blots, or PCR assays for identifying and quantifying the level of expression of CadF in a cell.

2. Construction of recombinant bacterial cell lines in which the activity of CadF protein is down-regulated or eliminated. Such cells may contain altered CadF coding sequences that result in the expression of a CadF protein that is not capable of carrying out its normal biological function.

3. The production of CadF proteins, which themselves are useful, e.g., in the production of vaccines, in the production of monoclonal and polyclonal antibodies, in diagnostic assays and the like.

Antisense CadF nucleotide sequences, that is, nucleotide sequences complementary to the non-transcribed strand of a CadF gene, may be used to block expression of mutant CadF expression. The use of antisense oligonucleotides and their applications have been reviewed in the literature (see, for example, Mol and Van der Krul, eds., *Antisense Nucleic Acids and Proteins Fundamentals and Applications*, New York, N.Y., 1992; which is incorporated by reference herein in its entirety). Suitable antisense oligonucleotides are at least 11 nucleotides in length and may include untranslated (upstream) and associated coding sequences. As will be evident to one skilled in the art, the optimal length of an antisense oligonucleotide depends on the strength of the interaction between the antisense oligonucleotide and the complementary mRNA, the temperature and ionic environment in which translation takes place, the base sequence of the antisense oligonucleotide, and the presence of secondary and tertiary structure in the target mRNA and/or in the antisense oligonucleotide. Suitable target sequences for antisense oligonucleotides regions in which DNA/RNA hybrids will prevent transport of mRNA from the nucleus to the cytoplasm, initiation factor binding sites, ribosome binding sites, and sites that interfere with ribosome progression. A particularly preferred target region for antisense oligonucleotide is the 5' untranslated (promoter/enhancer) region of the gene of interest. Antisense oligonucleotides may be prepared by the insertion of a DNA molecule containing the target DNA sequence into a suitable expression vector such that the DNA molecule is inserted downstream of a promoter in a reverse orientation as compared to the gene itself. The expression vector may then be transduced, transformed or transfected into a suitable cell resulting in the expression of antisense oligonucleotides. Alternatively, antisense oligonucleotides may be synthesized using standard manual or automated synthesis techniques. Synthesized oligonucleotides may be introduced into suitable cells by a variety of means including electroporation, calcium phosphate precipitation, liposomes, or microinjection. The selection of a suitable antisense oligonucleotide administration method will be evident to one skilled in the art. With respect to synthesized oligonucleotides, the stability of antisense oligonucleotide-mRNA hybrids may be increased by the addition of stabilizing agents to the oligonucleotide. Stabilizing agents include intercalating agents that are covalently attached to either or both ends of the oligonucleotide. Oligonucleotides may be made resistant to nucleases by, for example, modifications to the phosphodiester backbone by the introduction of phosphotriesters, phosphonates, phosphorothioates, phosphoroselenoates, phosphoramidates, or phosphorodithioates. Oligonucleotides may also be made nuclease resistant by synthesis of the oligonucleotides with alpha-anomers of the deoxyribonucleotides.

The invention further provides antibodies that specifically bind to CadF proteins. The production of non-human antisera or monoclonal antibodies (e.g., murine, lagormorph, porcine, equine) is well known and may be accomplished by, for example, immunizing an animal with CadF protein or peptides. If desired, an adjuvant may be included with the antigen during these immunizations. For example, CadF antibodies may be obtained by injecting a suitable animal host with the CadF polypeptide of SEQ ID NO: 2 as an antigen, or with CadF polypeptides encoded by the cadF-M129 or cadF-F38011 genes of SEQ ID NO: 5 and SEQ ID NO: 7. Such antibodies can be used to identify additional CadF proteins, which also are encompassed by this invention. The invention therefore includes antibodies capable of specifically binding a CadF polypeptide encoded by one of the nucleic acid molecules of SEQ ID NO: 1, SEQ ID NO: 5 and SEQ ID NO: 7. For the production of monoclonal antibodies, antibody producing cells are obtained from immunized animals, immortalized and screened, or screened first for the production of the antibody that binds to a CadF protein or peptides and then immortalized. It may be desirable to transfer the antigen binding regions (e.g., F(ab')2 or hypervariable regions) of non-human antibodies into the framework of a human antibody by recombinant DNA techniques to produce a substantially human molecule. Methods for producing such "humanized" molecules are generally well known and described in, for example, U.S. Pat. No. 4,816,397; which is incorporated by reference herein in its entirety. Alternatively, a human monoclonal antibody or portions thereof may be identified by first screening a human B-cell cDNA library for DNA molecules that encode antibodies that specifically bind to a CadF protein, e.g., according to the method generally set forth by Huse et al. (*Science* 246:1275–1281, 1989, which is incorporated by reference herein in its entirety). The DNA molecule may then be cloned and amplified to obtain sequences that encode the antibody (or binding domain) of the desired specificity.

The nucleic acid sequences, proteins and antibodies of the invention furthermore are useful in assays for determining the presence or amount of *C. coli* or *C. jejuni* in a test sample. In this regard, the nucleic acid sequences may by used as diagnostic probes, and the proteins and antibodies may be used in conventional competitive or direct sandwich assay formats using detectable labels, as is well known to those of ordinary skill in the art. In one of the assays of the invention, *C. coli* or *C. jejuni* is detected in a sample suspected of containing *C. coli* or *C. jejuni* by incubating a polyclonal or monoclonal antibody against CadF with the sample under conditions suitable for forming a complex between the antibody and a CadF polypeptide. The formation of an antibody-antigen complex in the incubated mixture may be detected by any of several means known to those skilled in the art, e.g., by observance of a flocculent precipitate, by physical separation of the complex, by colorimetric means, such as in ELISA, or by immunofluorescence. *C. coli* or *C. jejuni* is determined to be present in the sample if the antibody against CadF is found to have formed a complex with CadF after the antibody has been incubated with the sample.

Other assays for detecting *C. coli* or *C. jejuni* are based on nucleic acid probe hybridization, or on the amplification of specific DNA fragments using the polymerase chain reaction (PCR). In some embodiments, such assays utilize nucleic acid probes specific for the detection of *C. jejuni* or *C. coli*. Such probes involve isolated nucleic acid molecules that are at least 10 nucleotides in length, more preferably at least 12 nucleotides in length, and even more preferably at least 15 nucleotides in length, and that hybridize specifically with a cadF DNA molecule whose sequence is shown in SEQ ID NO: 1, SEQ ID NO: 5 and SEQ ID NO: 7. The specificity of this probe is such that the probe will not hybridize under similar hybridization conditions with genomic DNA of *Campylobacter hyointestinalis*, which has no CadF gene as determined by its lack of reactivity with antibody against CadF and the inability of its DNA to be amplified using the PCR primers CadF-F2B and CadF-R1B.

One skilled in the art can derive a variety of PCR primers useful for amplifyig all or part of cadF genes from the nucleotide sequences of SEQ ID NO: 1, SEQ ID NO: 5 and SEQ ID NO: 7. Thus, the invention provides various PCR primers that specifically amplify a DNA fragment from *C. jejuni* or *C. coli*. These primers are isolated nucleic acid molecules at least 10 nucleotides in length, or more preferably, at least 12 nucleotides in length, or even more preferably at least 15 nucleotides in length that hybridize to a cadF DNA molecule, such as a cadF molecule having a nucleotide sequence shown in SEQ ID NO: 1, SEQ ID NO: 5 or SEQ ID NO: 7, or their complements, but not to the DNA of *Campylobacter hyointestinalis*. The following sets of PCR primers are useful for amplifirg the cadF gene or portions thereof: Set 1: 5'-TTGAAGGTAA TTTAGATATG-3' (forward), 5'-CTAATACCTA AAGTTGAAAC-3' (reverse); Set 2: 5'-ATGAAAAAGT TATTACTATG TTTAGG-3' (forward), 5'-AGGATAAATT TAGCATCC-3'

(reverse); Set 3: 5'-TTGAAGGTAA TTTAGATATG-3' (forward), 5'-CTTCTTTTAC TTGTTCGGCT-3' (reverse); Set 4: 5'-TTGAAGGTAA TTTAGATATG-3' (forward), 5'-CATTGTGATT GTGTAGGTAC-3' (reverse). Primer Sets 3 and 4 are specific for the detection of *C. coli*, and do not amplify DNA from *C. jejuni*. It is understood that PCR primers other than the specific examples provided herein can be derived from the nucleotide sequences of SEQ ID NO: 1, SEQ ID NO: 5 and SEQ ID NO: 7, and their specificity confirmed as illustrated in Example 2.

The above-described PCR primers are useful in assays for determining the presence of *Campylobacter jejuni* or *Campylobacter coli* in test samples, e.g., food or patient samples. To perform such assays, DNA from a test sample is annealed with a pair of PCR primers that that flank a DNA fragment of known size and that are specific for *C. jejuni* or *C. coli*. Thus, these primers will not amplify DNA templates from a species that lacks a cadF gene, even if DNA from such a species is present in the sample. Examples of bacteria lacking a cadF gene are described in Example 2, and include, for example, *Campylobacter hyointestinalis*. Hybridization conditions used for these PCR reactions will vary according to the length and base composition of the particular primers, and methods for optimizing the hybridization and amplification conditions for a given set of PCR primers are well known in the art. *C. jejuni* or *C. coli* is determined to be present in the test sample if analysis of the PCR product reveals the presence of a DNA fragment having the expected size.

EXAMPLE 1

Identification and Characterization of a *Canmpylobacter jejuni* and *Campylobacter coli* 37 Kilodalton Fibronectin-binding Protein Experimental Procedures Bacterial Cultures

*C. jejuni* isolates F38011, M129, TGH1971, Np143 and *C. coli* M275 are clinical isolates. All Campylobacter isolates were cultured at 37° C. on Mueller-Hinton agar plates supplemented with 5% citrated blood (MH/blood) in Gas-Pak jars with CampyPak Plus packets (BBL Microbiology Systems, Becton Dickinson, Cockeysville, Md.). Cultures were passaged every 24 to 48 h. *Escherichia coli* (XL1-Blue, XL1-Blue MRF, and XLOLR), *Salmonella typhimurium*, and *Shigella dysenteriae* were cultured on Luria-Bertani (LB) agar plates (10g of Bacto-tryptone, 5 g of yeast extract, 10 g of sodium chloride, 15 g Bacto-agar per liter) in a 37° C. incubator. Plates were supplemented with ampicillin (50 µg/ml), kanamycin (50 µg/ml), or tetracycline (15 µg/ml) as appropriate.

Mammalian Cell Culture

Stock cultures of INT407 epithelial cells (human embryonic intestine, ATCC CCL 6) were obtained from the American Type Culture Collection. INT407 cells were routinely cultured in Eagle Minimal Essential Medium (EMEM) supplemented with 10% fetal bovine serum (FBS) at 37° C. in a humidified, 5% $CO_2$ incubator. For assays, a 24-well tissue culture tray was seeded with $1 \times 10^5$ cells/well. Plates were incubated for 18 h at 37° C. in a humidified, 5% $CO_2$ incubator. Prior to infection with bacteria, the cell monolayers were rinsed one time with EMEM containing 1% FBS.

Binding of *C. jejuni* to Mammalian Cells and Scanning Electron Microscopy

Infection of INT407 cell monolayers on thermonox coverslips with *C. jejuni* was done as described previously (Konkel et al., 1992). The infected cell monolayers were examined using a Joel 35CF scanning electron microscope.

Binding of *C. coli* to Immobilized Extracellular Matrix Proteins

Human plasma fibronectin, laminin, and vitronectin were purchased from Upstate Biotechnology (Lake Placid, N.Y.). Bovine serum albumin and ovalbumin were obtained from Sigma Chemical Co. The proteins were solubilized at a concentration of 1 mg/ml in sterile, deionized water. The ability of *C. coli* and *C. jejuni* to bind to these extracellular matrix components was determined using the protocol of Dawson and Ellen (Dawson and Ellen, 1990) with minor modifications. Forty µl of each of the protein solutions were evenly spread on plastic coverslips and air dried at 37° C. Unbound sites were blocked with 3% (w/v) BSA in phosphate-buffered saline (PBS). Aliquots (0.5 ml) c added to the coverslips and incubated at 37° C. for 1 h. The coverslips were then rinsed 30 times in PBS. Bound bacteria were stained with acridine orange and visualized by fluorescence microscopy using a Leitz fluorescence microscope at 400×magnification. For each coverslip, the number of bacteria in each of three randomly chosen fields were counted.

Binding of $^{125}$I-Fn to *C. jejuni*

Fn was labeled with $^{125}$I-NaI using the Iodogen method (Fraker and Speck, 1978). Briefly, 100 µg of Fn (1 mg/ml) was added to Iodogen-coated glass tubes containing 100 µCi of carrier-free $^{125}$I-NaI (17.4 Ci/mg; New England Nuclear, Boston, Mass.). The tubes were incubated for 10 min on ice and unincorporated label removed by centrifugation through a Bio-Spin 6 column (Bio-Rad Laboratories, Hercules, Calif.). The labeling procedure typically resulted in specific radioactivity of $1-2 \times 10^6$ cpm/µg of Fn. The binding of soluble Fn to *C. jejuni* was determined by incubation of various amounts of $^{125}$I-Fn (specific radioactivity adjusted to $5 \times 10^3$ cpm/µg) with $5 \times 10^7$ cfu of *C. jejuni* in a total volume of 0.5 ml of PBS containing 0.1% (w/v) BSA in microcentrifuge tubes for 1 hour at room temperature with gentle agitation. The tubes were preincubated with 3% BSA at 4° C. overnight to reduce nonspecific binding of the $^{125}$I-Fn to the tubes. After incubation, the bacteria were pelleted by centrifugation, washed three times with PBS, and resuspended in PBS. The amount of radioactivity in the tube was determined by gamma spectrometry. Background or non-specific binding of $^{125}$I-Fn to the tubes was routinely determined to be less than 5% of the total counts. Specific binding was assessed by determining the amount of unadjusted $^{125}$I-Fn ($1 \times 10^6$ cpm/µg) bound in the presence of 50-fold molar excess of unlabeled Fn. In some experiments, *C. jejuni* (10 ml suspension of approximately $5 \times 10^8$ cfu/ml) were treated with proteases (1 mg/ml of trypsin and 100 µg/ml of proteinase K in 0.1 M Tris pH 8.0 for 30 minutes at 37° C.) or 10 mM sodium meta-periodate (in 0.5 M sodium acetate pH 4.5 at room temperature for 15 minutes) (Konkel and Joens, 1989). Phenylmethylsulfonyl fluoride was added to protease treated samples at a final concentration of 1 mM to quench the reactions. Following treatment, bacteria were washed twice with PBS prior to determination of Fn binding.

Preparation of Bacterial Omp Extracts

Omp extracts were prepared as described by De Melo and Pechere with minor modifications (De Melo and Pechere, 1990). Briefly, bacteria were pelleted by centrifugation, washed once with PBS at 4° C., and suspended in 10 mM sodium phosphate (pH 7.4). Bacterial suspensions were then sonicated on ice five times (30 s each) with a 30 s cooling period between each pulse. Whole cells were removed by centrifugation at 6,000×g for 20 min. Crude membranes were pelleted by centrifugation at 100,000×g for 2 h, suspended in 10 mM Tris pH 7.5, and treated with sodium N-lauryl-sarcosine (pH 7.5) at room temperature on a platform rocker for 30 min. Following incubation, the suspensions were subjected to centrifugation at 100,000×g for 2 h at 15° C. The pellets were washed once with 50 mM Tris pH 7.5, suspended in the same buffer, and stored at −20° C.

Binding of Fn to Immobilized Omps

Omp extracts of C. jejuni and E. coli were separated by sodium dodecyl sulfate-polyacrylamide gel electrophoresis (SDS-PAGE) in 12.5% resolving gels and electrophoretically transferred to polyvinylidene fluoride (PVDF) membranes (Immobilon P; Millipore Corp., Bedford, Mass.). The membranes were washed three times in PBS and incubated in PBS pH 7.4/0.01% Tween-20 (PBS/Tween) containing 3% (w/v) BSA for 1 h at room temperature. The membranes were then incubated with 10 µg of $^{125}$I-Fn for 18 h at 4° C. with gentle agitation, washed 10 times in PBS/Tween and then water, and air dried. Bound $^{125}$I-labeled Fn was detected by autoradiography using Kodak X-Omat film. Nonspecific binding was determined by including 100-fold molar excess of unlabeled Fn in the incubation mixture.

Alternatively, Fn was labeled with sulfo-NHS-biotin using an EZ-Link Sulfo-NHS-Biotinylation Kit (Pierce). Briefly, Fn (1 µg) was mixed with sulfo-NHS-biotin (0.3 µg) and the mixture incubated for 45 min at room temperature. The biotinylated Fn was then purified by passage over a dextran desalting column (Pierce). Fractions containing biotinylated-Fn were combined and concentrated with a Centricon-10 (Amicon, Beverly, Mass.). After SDS-PAGE and transfer of C. coli omps to PVDF membranes, the membranes were incubated with 0.4 µg of biotinylated-Fn in PBS containing 5% nonfat dried milk for 90 min at room temperature. Membranes were then washed three times with PBS and incubated with peroxidase-conjugated avidin in PBS containing 5% nonfat dried milk. Following a 90 min incubation at room temperature, the membranes were again washed three times with PBS. The peroxidase-conjugated avidin linked to bound Fn was detected using 4-chloro-1-naphthol (Sigma) as the chromogenic substrate.

Preparation of the Rabbit Antiserum to the 37 kDa Omp and Immunoblotting

C. jejuni M129 omp extracts were separated by SDS-PAGE, stained with Coomassie brilliant blue-R250, and the 37 kDa protein band excised from the gel. Purified protein was recovered from the excised-gel slices using a protein electro-elution apparatus as described by the manufacturer (Bio-Rad Laboratories, Hercules, Calif.). Polyclonal antiserum against the C. jejuni 37 kDa protein was produced in a female New Zealand White rabbit by subcutaneous injection of 100 µg of the immunogen in complete Freund's adjuvant. A booster injection of 50 µg in incomplete Freund's adjuvant was given after four weeks. Blood was collected prior to first and second immunizations, and two weeks after the second immunization. The collected serum was stored at −20° C. For electrophoresis, bacterial whole-cell extracts (an equivalent of 0.1 $OD_{600}$ units) and omp extracts (20 µg/ml) were solubilized in single strength electrophoresis sample buffer and incubated at 95° C. for 5 min. Proteins were separated in SDS-12.5% PAGE minigels using the discontinuous buffer system described by Laemmli (Laemmli, 1970) and electrophoretically transferred to PVDF membranes. The membranes were incubated for 18 h at 4° C. with a 1:250 dilution of the rabbit anti-C. jejuni 37 kDa serum in PBS/Tween-20 containing 20% FBS. Bound antibodies were detected using peroxidase-conjugated goat-anti-rabbit IgG and 4-chloro-1-napthol (Sigma) as the chromogenic substrate.

Construction of C. coli Genomic Expression Libraries and Immunoscreening

C. coli M275 chromosome DNA was isolated as described previously (Marconi etal., 1993). Campylobacter genomic-phage libraries were constructed by ligation of C. coli chromosomal DNA partially digested with either Sau3AI or Bgl II into the BamH I site of the lambda ZAP Express insertion vector (Stratagene, La Jolla, Calif.). The ligated products were precipitated and then packaged into phage heads without amplification using a Gigapack II Gold packaging extract (Stratagene).

Phage plaques were transferred to Duralose-U.V. membranes (Stratagene) and incubated with a 1:250 dilution of the anti-37 kDa rabbit serum in PBS/Tween-20 with 20% FBS. Bound antibodies were detected using horseradish peroxidase-conjugated goat anti-rabbit IgG (Organon Teknika Corp., West Chester, Pa.) and 4-chloro-1-naphthol (Sigma) as the chromogenic substrate. Membranes were also screened with $^{32}$P-end labeled or $^{32}$P-nick-translated probes using buffers and conditions described previously (Marconi et al., 1993). Plaques giving rise to a positive signal were picked and rescreened. High-titered phage stocks were then prepared and the pBK-CMV phagemid was rescued using the in vivo excision protocol outlined by the supplier. The inserts contained within the pBK-CMV phagemid vector were amplified by the polymerase chain reaction using T3 and T7 oligonucleotide primers and Taq DNA polymerase (Promega, Madison, Wis.). DNA amplification was preformed using an automated DNA thermal cycler (MJ Research, Inc.) for 30 cycles under the following conditions: 95° C. for 1 min, 50° C. for 1 min, 72° C. for 3 min. Following amplification, the products were precipitated, washed once with 70% ethanol, and examined by agarose gel electrophoresis.

Isolation of Isogenic C. jejuni CadF Mutants

The cadF gene in C. jejuni F38011 was disrupted by homologous recombination via a single crossover event between the cadF gene on the chromosome and an internal fragment of the cadF gene on a suicide vector. A 696 bp internal fragment of the cadF gene from C. jejuni F38011 was amplified by the polymerase chain reaction and cloned into the pCRII cloning vector (TA Cloning System, Invitrogen, San Diego, Calif.). The cloned insert was excised by restriction endonuclease digestion with EcoR I, gel-purified, and ligated into the pBluescript SK$^+$ (pBSKII$^+$) containing a Campylobacter kanamycin resistance gene. The pBSKII$^+$ vector was digested with EcoR I and treated with calf intestinal alkaline phosphatase prior to ligation. The resultant plasmid was introduced into C. jejuni F38011 by electroporation and acted as a suicide vector to deliver the internal fragment of the cadF gene into the C. jejuni chromosomal gene through allelic exchange. Potential insertional mutants were identified by the acquisition of kanamycin resistance.

Other Analytical Procedures

Two-dimensional gel electrophoresis was performed as described previously (Konkel et al., 1993b). Protein concentrations were determined using the bicinchoninic acid (BCA) method using a kit from Pierce and BSA as the standard (Smith et al., 1985). DNA sequencing was performed using a double-stranded DNA cycle sequencing kit according to the supplier's instructions (Life Technologies Inc.). Sequencing primers were synthesized by Ransom Hill Bioscience, Inc. (Ramona, Calif.).

Results

Binding of C. jejuni and C. coli to Cells and to the Extracellular Matrix

The effects of various parameters on the ability of C. jejuni to bind to eukaryotic cells have been previously studied (Konkel et al., 1992). Although temperature (40° C., 25° C., and 37° C.) was found to have little effect on the numbers of C. jejuni bound to INT407 cells, scanning electron microscopy of C. jejuni-infected cells incubated at 4° C. for 30 minutes revealed that some of the eukaryotic cells became round and began to detach from the substrate leaving behind long retraction fibers. These finger-like projections were spaced regularly around the edge of the cell body and allowed the cell to remain attached to the substrate through flattened pads termed adhesion plaques. Many C. jejuni were observed preferentially bound to the retraction fibers.

As the basement membrane underlying an epithelial cell is rich extracellular matrix components (EMC) including fibronectin (Fn), laminin, and vitronectin, one C. jejuni isolate (TGH1971) and one C. coli isolate (M275) were tested for their ability to bind to these matrix components in accord with the coverslip binding assay described above. E. coli HB 101 served as a control. The results of these assays are presented in Table 1. The values in Table 1 represent the mean number of bacteria bound in each of three randomly-chosen fields±standard deviation. In Table 1, "ND" means "not determined." As shown in Table 1, both of the Campylobacter isolates tested bound to Fn in numbers significantly greater than that of the E. coli control. The one C. jejuni isolate tested for binding to the laminin or vitronectin-coated coverslips did not bind, nor did either of the two Campylobacter isolates bind significantly to the control ovalbumin-coated coverslips. Binding to Fn was not reduced when the peptide Arg-Gly-Asp (R-G-D), which is a consensus eukaryotic cell surface Fn binding-site, was added to the bacterial suspension during the binding step.

In other experiments, the ability of intact bacterial cells to bind to soluble $^{125}$I-Fn was tested as described above. The $^{125}$I-Fn was found to bind to C. jejuni, and the binding was found to be saturable at a concentration of approximately 50 $\mu$g/ml. Approximately 50% of the binding of $^{125}$I-Fn to C. jejuni was determined to be specific by competition experiments in which a 50-fold molar excess of unlabeled Fn was present during the binding step. In these experiments, the background of non-specific binding of $^{125}$I-Fn to the tubes was determined to be less than 5% of the bacteria-bound ligand.

TABLE 1

Binding of C. jejuni and C. coli Cells to Immobilized Fn, Laminin, Vitronectin, and Ovalbumin
Number of Bacteria Bound

| Isolate | Fibronectin | Laminin | Vitronectin | Ovalbumin |
|---|---|---|---|---|
| TGH1971 | 149.0 ± 8.5 | 7.0 ± 10.4 | 0 | 6.7 ± 3.2 |
| M275 | 228.7 ± 46.5 | ND | ND | 10.3 ± 6.7 |
| E. coli HB101 | 30.6 ± 5.9 | ND | ND | 4.7 ± 40 |

ND, not determined

In other experiments, the treatment of C. jejuni with either trypsin (1 mg/ml) or proteinase K (100 $\mu$g/ml) was shown to reduce the binding of $^{125}$I-Fn to less than 20% of control levels (Table 2). In contrast, sodium meta-periodate (10 mM), which modifies carbohydrate groups, had little effect on Fn binding. For the experiments whose results are shown in Table 2, the amounts of $^{125}$I-Fn bound were calculated by dividing the observed radioactivity bound (cpm bound) by the specific radioactivity ($5\times10^3$ cpm/$\mu$g); the ng values shown in Table 2 are the means of triplicate determinations±standard deviation. Collectively, the data in Tables 1 and 2 suggest that the primary C. jejuni Fn-binding constituent(s) is a surface exposed protein.

TABLE 2

Effect of Proteases and Chemical Modification on the Binding of Fn to C. jejuni

| Treatment | ng Fn bound | (% control) |
|---|---|---|
| Control | 380 ± 100 | (100) |
| Trypsin | 54 ± 8 | (14.2) |
| Proteinase K | 17 ± 2 | (4.5) |
| Sodium meta-periodate | 270 ± 40 | (71.1) |

Identification of a 37 kDa Fn-binding Omp

Ligand immunoblot assays using $^{125}$I-Fn were performed to identify potential Fn-binding proteins in C. jejuni omp extracts. The extracts were separated by SDS-PAGE and transferred to PVDF membranes as described above. One membrane was incubated with $^{125}$I-Fn, and another with both $^{125}$I-Fn and a 100-fold excess of unlabeled Fn. Although $^{125}$I-Fn bound to several proteins in the extracts, only one protein bound Fn specifically as judged by the selective reduction of reactivity associated with this band in the presence of excess unlabeled Fn. This protein had an apparent molecular mass of 37 kDa and was designated CadF, for Campylobacter adhesion to Fn. De Melo and Pechere (1990) have previously observed a protein of about this size that appeared to bind to intact cultured epithelial cells.

An antiserum was prepared in rabbits against the gel-purified 37 kDa omp (CadF). This antiserum was used for immunoblotting to analyze 14 isolates of C. jejuni for the presence of CadF. These isolates were obtained from human and non-human sources. The C. jejuni strains analyzed for this set of experiments were: F38011; 81116; 43466; 33560; 78–42; M129; 87–95; 78–27; M3143; KLC100; KLC101; KLC102; KLC105; and KLC106. For these analyses, 25 $\mu$g/lane of whole-cell extracts were separated on 12.5% SDS-PAGE gels, transferred to PVDF membranes, and reacted with a 1:250 dilution of rabbit anti-CadF antiserum. Bound antibodies were detected as described above.

Results showed that an immunoreactive protein with an apparent molecular mass of 37 kDa and another immunoreactive band of 32 kDa were present in whole-cell lysates all 14 C. jejuni isolates as well as in both C. coli isolates that were also tested. These findings indicate that CadF is conserved with respect to size and antigenicity among Campylobacter isolates. Similar immunoblot analyses showed that an immunoreactive band was not found in whole-cell or omp extracts of Salmonella typhimurium or Shigella dysenteriae when antiserum against CadF was used. Trypsin or proteinase K treatment of intact C. jejuni abrogated the immunoreactivity of CadF with the rabbit anti-37 kDa serum as judged by immunoblot analyses, indicating that CadF is surface exposed. These immunoblot analyses of Campylobacter whole-cell extracts with the rabbit anti-37 kDa serum revealed also a second immunoreactive species with an apparent molecular mass of 32 kDa.

Previous studies have shown that several outer membrane proteins, such as ompA and phospholipase A from E. coli, exhibit altered electrophoretic mobilities when the cells were solubilized at different temperatures. Heat modifiability is characteristic of outer membrane proteins and reflects the protein's conformational state (Bolla et al., 1995). To determine if CadF is heat modifiable, C. jejuni whole-cell extracts were solubilized in sample buffer containing SDS and heated to 60° C. for 30 min or 100° C. for five minutes, then subjected to gel electrophoresis and immunoblotting. The 37 kDa immunoreactive band was prominent when whole-cell extracts of C. jejuni were boiled for five minutes. In contrast, solubilization of samples at 60° C. resulted in the predominance of a 32 kDa immunoreactive band, indicating that CadF exhibits heat modifiable electrophoretic migration. Presence of the 37 kDa and 32 kDa bands at the different temperatures was not dependent on the presence of 2-mercaptoethanol in the solubilization buffer. Higher molecular weight species, which would indicate the presence of higher order oligomeric complexes, were not detected using the rabbit anti-37 kDa serum when C. jejuni whole-cell lysates were separated by non-denaturing gel electrophoresis.

Convalescent antisera from C. jejuni-infected individuals (n=5) was used in immunoblot analysis to determine whether reactivity against CadF was present. For these analyses, extracts of C. coli M275 omps were separated in 12.5% SDS-PAGE gels, and transferred electrophoretically to seven PVDF membranes. One membrane as a control was reacted with a 1:250 dilution of the above-described rabbit anti-CadF antiserum, and five were reacted with 1:50 dilutions of convalescent serum from different C. jejuni infected patients. As an additional control, one membrane was incubated with a 1:50 dilution of serum from a non-infected individual. This last membrane was negative, but all the remaining membranes, after being developed, showed a 37 kDa protein. Thus, all five of the Campylobacter-infected patients appeared to possess antibodies that were reactive with CadF.

Cloning and Sequencing of the Gene Encoding CadF

The rabbit anti-37 kDa serum was used to screen several Campylobacter genomic expression libraries and several immunoreactive clones were identified. One of the recombinant plasmids obtained, designated pMEK6005, contained an insert of approximately 2.5 kb. Analysis of whole-cell lysates of E. coli transformants harboring pMEK6005 exhibited immunoreactivity only when the bacteria were grown in the presence of isopropyl-B-D-thiolgalacto-pyranoside. Further sequence analysis confirmed that an open reading frame (orf) was continuous and in frame with the β-galactosidase gene of the pBK-CMV vector, thereby indicating that the immunoreactive band was a fusion protein encoded by a gene under control of the lac promoter of the vector. Oligonucleotide probes generated using the sequence of the insert contained within the pMEK6005 recombinant plasmid were used to identify nine more recombinant phage clones.

The inserts contained within these clones were amplified by the polymerase chain reaction and subjected to sequence analysis. All clones contained only a portion of the coding sequence for CadF and only one clone contained the 5' end of the gene. Sequencing of overlapping gene inserts revealed an orf of 981 nucleotides that is capable of encoding a protein of 326 amino acids with a calculated molecular mass of 36,872 Da (SEQ ID NO: 1). The DNA and protein sequence data shown in SEQ ID NO: 1 have been assigned Genbank Accession No. U87559. The orf of the nucleotide sequence in SEQ ID NO: 1 begins with an ATG and is terminated by two in-frame stop codons (TAA and TGA).

Examination of the amino terminus of the deduced CadF amino acid sequence revealed a potential signal peptide 16 residues in length (Von Heijne, 1985). The putative signal sequence is composed of two positively charged residues (Lys-Lys) at the second and third positions followed by a core of predominately hydrophobic residues. The amino-terminal amino acid sequence of the mature CadF protein was determined after separation by SDS-PAGE and electrophoretic transfer to PVDF membranes to be: A-D-N-N-V-K-F-E-I-T-P-X-L-N (SEQ ID NO: 19). This sequence corresponds to residues 17 through 30 of the deduced amino acid sequence and indicates that the predicted 16 residue signal peptide is removed during maturation of the protein. The calculated molecular mass of the mature CadF protein is 35,168 Da, which is similar to the mass estimated by SDS-PAGE.

The deduced amino acid sequence of C. coli M275 CadF was compared with the protein sequences found in the database maintained by the National Center for Biotechnology Information (NCBI) and was found to exhibit greatest similarity to the outer membrane protein porin F (OprF) from Pseudomonas spp. The CadF sequence exhibited 29% identity (53% similarity) to OprF from P. aeruginosa and 28% identity (52% similarity) to OprF from P. fluorescens. Interestingly, purified OprF from P. fluorescens displays in vitro binding to plant roots and is heat-modifiable (De Mot et al., 1992; De Mot and Vanderleyen, 1991). It also has been demonstrated by Logan and Trust (1982) that an outer membrane protein with an apparent molecular mass of 37 kDa is surface exposed using surface radioiodination of intact C. jejuni. CadF may be identical to the 37 kDa surface protein observed by Logan and Trust.

Fn-binding Activity of C. jejuni Mutants Containing Insertions in CadF

To investigate the binding properties of CadF, two kanamycin resistant C. jejuni isogenic mutants, designated mutCadF1 and mutCadF9, containing insertional disruptions of the cadF gene were isolated. Omp extracts of mutCadF9 were found to lack the 37 kDa protein species corresponding to CadF as follows. Extracts of the parent wild-type C. jejuni (strain F38011) and the mutants were subjected to two-dimensional gel electrophoresis, using isoelectric focusing in the first dimension, and 12.5% acrylanide in the second dimension. The separated proteins were either stained with Coomassie brilliant blue R-250 or transferred to PVDF membranes and reacted with a 1:250 dilution of rabbit anti-37 kDa serum. The results indicated that no 37 kDA protein was thus detectable in the extracts from either of the mutants.

The mutant bacteria were tested further for their ability to bind to Fn immobilized on coverslips as described above. For both mutants, the binding was reduced by more than 60% as compared with the parental C. jejuni strain and approximated the binding exhibited by a laboratory strain of E. coli. These results are shown in Table 3. Finally, ligand immunoblotting experiments using biotinylated Fn as described above showed that mutCadF9 also failed to bind Fn. For these latter experiments, outer membrane proteins of C. jejuni F38011 and an isogenic mutant (mut CadF9) were separated in 12.5% SDS-PAGE gels, transferred to polyvinyl fluoride membranes, and reacted either with antiserum against CadF or with biotinylated Fn. Bound biotinylated Fn was visualized as described above. Results indicated that while the wild-type C. jejuni extracts contained a protein that bound to biotinylated Fn, the mutant did not, thus providing further evidence that CadF plays an essential functional role in binding Fn.

TABLE 3

Binding Activity of C. jejuni CadF Mutants to Fn on Coverslips
Number of Bacteria Bound

| Strain | Fn | BSA |
| --- | --- | --- |
| F38011 (parent) | 178 ± 39 | 31.5 ± 4.4 |
| mutCadF1 | 66.5 ± 18.5* | 2.1 ± 19.6 |
| mutCadF9 | 28.0 ± 2.9* | 24.8 ± 9.8 |
| E. coli XL1 Blue | 40.3 ± 4.6* | 17.5 ± 3.5 |

Binding assays were performed as described above. The values represent the mean number of bacteria bound in four randomly chosen fields ± standard deviation.
*Denotes that the value was significantly different (p < 0.001) from that obtained using the parental strain, F38011. Statistical comparisons were done using analysis of variance and independent t-tests with the Bonferroni correction for multiple comparisons. The binding of two mutants to either Fn or BSA did not differ significantly from that of the E. coli XL1 Blue.

Thus, these studies indicate that CadF is an adhesin that promotes the binding of C. jejuni to ECM and, in particular, to Fn, which is a large, multifunctional glycoprotein that promotes numerous adherence functions in mammalian cells. Binding to Fn has been widely implicated as a primary means of attachment to tissue surfaces by various bacterial pathogens. Without first binding to host cells, pathogenic bacteria cannot invade the cell, hence the expression of CadF is believed to be a prerequisite for virulence in C. coli and C. jejuni.

The carboxyl terminal region of CadF also possesses an alpha-helical consensus motif ($NX_2LSX_2RAX_2VX_3L$) that has been proposed to be involved in the noncovalent association of outer membrane proteins with peptidoglycan (Koebnik, 1995). This consensus motif has previously been identified in a number of proteins, including the Omp 18 from C. jejuni (Konkel et al., 1996), PAL of E. coli (Chen and Henning, 1987; Lazzaroni and Portalier, 1992), Omp16 from Brucella abortus (Tibor et al., 1994), P6 of Haemophilus influenzae (Deich et al., 1988; Nelson et al., 1988), PplA of Legionella pneumophila (Engleberg et al., 1991; Ludwig et al., 1991), and OmpA from Enterobacteriaceae.

It is noteworthy that the rabbit anti-CadF serum employed in these studies did not inhibit the binding of C. jejuni to Fn or to cultured cells. However, immunofluorescence microscopy with viable and paraformaldehyde-fixed C. jejuni incubated with the rabbit antiserum revealed that this particular antiserum did not react with intact organisms, and thus it may not recognize native CadF present in the outer membrane. This is not altogether surprising, given that the antibodies used here were raised against denatured CadF, i.e., CadF that had been eluted from SDS gels. Thus, this antibody may be active only against internal epitopes or epitopes that are exposed only under denaturing conditions. This supposition was confirmed by later experiments in which C. jejuni and C. coli did react with this same antiserum after fixation with methanol, which permeabilizes bacteria, often exposing otherwise inaccessible epitopes in their outer membranes.

Of the 11 clones identified by screening several different C. coli or C. jejuni genomic libraries with the rabbit anti-37 kDa antibody and labeled primers, not one contained the entire coding sequence for CadF. This finding may indicate that full-length CadF is toxic to E. coli, and thus it may be necessary to utilize a yeast, or other expression system to obtain full-length recombinant CadF protein. It is noteworthy in this regard that the OprF protein of Pseudomonas species, specifically P. aeruginosa, has been reported to have pore-forming activity (Bellido et al., 1992; Nikaido et al., 1991). Thus, protein derived from these CadF clones could not be used us to establish directly that CadF mediates binding to Fn by viable cells. However, indirect evidence of a role for CadF in adherence is provided by the demonstration that mutants of C. jejuni lacking the cadF gene and protein exhibited markedly reduced binding to Fn as described above. Accordingly, CadF appears to be the primary Fn-binding component on the surface of C. jejuni and C. coli.

CadF may play an important role in establishing C. jejuni and C. coli colonization of the gastrointestinal tract. Several groups have independently shown that a number of Campylobacter isolates bind to Fn. Furthermore, Fn is present at regions of cell-to-cell contact in the gastrointestinal epithelium, thereby providing a potential bacterial binding site (Quaroni et al., 1978).

EXAMPLE 2

Identification of the Enteropathogens
Campylobacter Jejuni and Campylobacter Coli by
Polymerase Chain Reaction, Immunoblot Analysis,
and Indirect Immunofluorescence Experimental Procedures Bacterial Isolates and Growth Conditions The bacterial isolates used in this study are listed in Table 4. C. jejuni, C. coli, Campylobacter hyointestinalis, and Helicobacter pylon isolates were cultured on Mueller-Hinton agar plates containing 5% citrated bovine blood (MH/blood) in a 11.5% $CO_2$ incubator at 37° C. All isolates were passaged every 24 to 48 h. Pseudomonas aeruginosa, Shigella flexneri, Salmonella typhimurium, and Escherichia coli were cultured on Luria-Bertani (LB) agar plates (10 g of Bacto-Tryptone, 5 g of yeast extract, 10 g of sodium chloride, and 15 g of Bacto-Agar per liter) in a 37° C. incubator.

TABLE 4

Bacterial Isolates Used in this Study

| Strain | Serotype | Biotype | Source or Reference |
| --- | --- | --- | --- |
| C. jejuni Isolates | | | |
| 33560 | 99 | I | ATCC |
| F38011 | 90 | I | AZ |
| M129 | 36 | I | AZ |
| H70100 | 32 | II | AZ |
| M95 | 7 | I | AZ |
| M98 | UT | II | AZ |
| M125 | UT | II | AZ |
| M128 | 1 | I | AZ |
| M369 | Rough, UT | I | AZ |
| M521 | 7 | I | AZ |
| M48789 | 5 | II | AZ |
| W52400 | 77 | II | AZ |
| X34578 | UT | II | AZ |
| St. Joseph | Rough, UT | I | AZ |
| St. M 3143 | UT | I | AZ |
| St. M F1474 | 36 | I | AZ |
| St. M T6644 | 36 | I | AZ |
| St. M W726 | 16 | I | AZ |
| UMC T1393 | 18 | III | AZ |
| T8531 | 36 | II | AZ |
| TGH3611 | 9 | II | AZ |
| KLC 100 | 2 | II | WA |
| KLC 101 | 99 | I | WA |
| KLC 102 | 36 | II | WA |
| KLC 106 | 76 | I | WA |
| KLC 108 | ND | ND | WA |
| KLC 109 | 36 | II | WA |

TABLE 4-continued

Bacterial Isolates Used in this Study

| Strain | Serotype | Biotype | Source or Reference |
|---|---|---|---|
| KLC 110 | 7 | I | WA |
| KLC 111 | 4 | II | WA |
| KLC 112 | 36 | I | WA |
| KLC 114 | 6 | II | WA |
| E95-412 (blood isolate) | 2 | I | MN |
| E96-1009 (blood isolate) | 18 | I | MN |
| E97-2653 (blood isolate) | 36 | I | MN |
| E97-2796 | UT | II | MN |
| E97-2805 | 38 | II | MN |
| E97-2845 | 2 | I | MN |
| 78-27 | 1 | I | M. Blaser |
| 81116 | 6 | III | L. Tompkins |
| 81176 | 5 | I | L. Tompkins |
| *C. coli* Isolates | | | |
| M275 | 29 | I | AZ |
| T1138 | 12 | II | L. Tompkins |
| T1631 | ND | ND | L. Tompkins |
| 2144 | 97 | I | L. Tompkins |
| T2234 | 105 | I | L. Tompkins |
| INN-18383 | 105 | I | L. Tompkins |
| Other Isolates | | | |
| *Campylobacter hyointestinalis* 35217 | | | ATTC |
| *Helicobacter pylori* 43504 | | | ATTC |
| *Pseudomomonas aeruginosa* PA01 | | | ATTC |
| *Shigella flexneri* 13313 | | | ATTC |
| *Salmonella typhimurium* 85-102840 | | | H. Olander |
| *Escherichia coli* H30 | | | D. Francis |

UT = untypable; ND = not done.

Hippurate Hydrolysis Test. Hippurate hydrolysis, performed using the rapid method of Hwang and Ederer (1975), was used to discriminate between *C. jejuni* (hippurate positive) and *C. coli* (hippurate negative). Briefly, a loopful of *C. jejuni* and *C. coli*, harvested from 24 h culture plates, was added to 3 ml of 1% sodium hippurate (Sigma Chemical Com., St. Louis, Mo.) and incubated for 2 h at 37° C. in a 11.5% $CO_2$ incubator. After 2 h, 0.5 ml of 3.5% ninhydrin (Sigma) was added to the tubes and the tubes incubated for one more hour as before. A positive hippurate test was recorded as development of a deep purple color indicating that glycine was produced from the hydrolysis of hippurate by the enzyme hippuricase, whereas a negative showed no color formation. A positive control was *Streptococcus agalactiae*, while a negative control was *Streptococcus pyogenes*—rapid H2S test. The rapid H2S test used was originally described by Skirrow and Benjamin (1980) with modifications made by Lior (1984). A semisolid agar base was prepared which contained the following: brucella broth (Difco Laboratories, Detroit, Mich.), 2.9 g; $Na_2HPO_4$ (anhydrous), 0.118 g; $KH_2PO_4$ (anhydrous), 0.023 g; and select agar (Gibco BRL, Gaithersburg, Md.), 0.2 g; dissolved in 97 ml $dH_2O$. The base media was autoclaved and then cooled to 48° C. The following were prepared as 10% solutions, filter sterilized, and mixed in the following sequence: 1 ml of ferrous sulphate was added to 1 ml of sodium metabisulfite, mixed and then added to 1 ml of sodium pyruvate. The entire 3 mls was then added to the cooled base media, mixed, and 3 ml of the complete media was added to sterile screw-capped tubes (13 by 100 mm). A loopful of bacteria was suspended halfway through the each 3 ml tube of media. The inoculated tubes were incubated at 37° C. in a 11.5% $CO_2$ incubator for 3 h. A positive result was the formation of a black precipitate around the organisms, whereas a negative result showed no blackening. A positive control was *Salmonella tphimurium*, while *Shigella flexneri* served as a negative control. To ensure the reproducibility of the results, the rapid $H_2S$ test was also performed at the National Lab for Enteric Pathogens, Laboratory Centre for Disease Control, Ottawa, Ontario.

DNase Hydrolysis Test. DNAse test agar medium (Difco Laboratories, Detroit, Mich.) was prepared according to the manufacturers instructions. A line of *C. jejuni* was streaked on the agar and plates incubated at 37° C. in an 11.5% $CO_2$ incubator for 24 h. The growth was then scraped from the surface of the agar plates and the plates flooded with 0.1N HCl to precipitate the DNA from the media. A positive result was a clear zone beneath and around the site of bacterial growth. A positive control for this test was *Serratia marcescens*, while a negative control was *Enterobacter aerogenes*. To ensure the reproducibility of the results, DNase testing was also performed using the method of Lior and Patel (1987) at the National Lab for Enteric Pathogens, Laboratory Centre for Disease Control, Ottawa, Ontario.

Pulsed-Field Gel Electrophoresis (PFGE). Pulse-field gel analysis was performed as outlined by Chang and Taylor (1990) with minor modifications. *C. jejuni* were harvested from MH/blood agar plates in TE buffer (50 mM Tris, 2 mM EDTA pH 8.0) and cell densities adjusted to an $OD_{600}$ of 2.0. Four hundred $\mu l$ of each bacterial suspension added to 700 $\mu l$ of 1.3% low melting point agarose (Bio-Rad Laboratories, Hercules, Calif.) that had been boiled and cooled to 50° C. Exactly 100 $\mu l$ of the mixture was pipetted into agarose gel molds which were presized to fit the wells of the PFGE combs. After the agarose solidified, the agarose blocks were removed from the molds and incubated in 1 ml of ESP buffer (500 mM EDTA, 1% N-lauroyl sarcosine, 0.1 mg/ml Proteinase K) at 50° C. for 48 h. Following digestion, the agarose blocks were washed two times in TE plus 1 mM phenylmethylsulfonyl fluoride PMSF) for 20 min at 37° C. and then two more times in TE without PMSF for 20 min at 37° C. Each agarose block, containing 4–8 $\mu g$ of DNA per block, was then preincubated in 1 ml of 1× restriction endonuclease buffer for 1 h at 37° C. Following preincubation, the buffer was removed and replaced with 150 $\mu l$ of 1× restriction endonuclease buffer containing 2 $\mu l$ of the restriction endonuclease enzyme. The reactions were incubated at 37° C. for 12 h. Immediately following incubation, the agarose plugs were loaded onto a pulsed-field gel. Restricted DNAs were separated in 1% agarose (Pulsed-Field Certified, Bio-Rad Laboratories, Hercules, Calif.) which had been prepared with 0.5×TBE (0.089 M Tris base, 0.089 M boric acid, 0.002M EDTA, pH 8.0), in 0.5×TBE running buffer. Typical run parameters consisted of a reorientation angle of 120 degrees with a constant voltage of 180 v and a constant temperature of 14° C. Actual run and pulse times varied depending on the restriction endonuclease employed, the sizes of the restricted fragments, and on the region of the gel determined to be of greatest interest. For the enzyme SalI, a run time of 23 h and a ramped pulse time of 15–105 s was used, whereas for the enzyme KpnI, a run time of 20 h and a ramped pulse time of 5–75 s was used. After runs were completed, the gels were stained for 1 h in μg ml/1 ethidium bromide in deionized water and then destained in water for 1 h.

Polymerase Chain Reaction and Analysis of Amplified Products. PCR was performed with a few bacterial colonies, harvested from agar plates with a sterile plastic inoculating loop, and suspended in 200 μl of water. Amplification reactions were performed in a volume of 100 μl containing 10 μl of the bacterial suspension, 10 μl of 10×PCR buffer minus Mg, 8 μl of a mixture of the four deoxyribonucleotides (final concentration; 2.0 mM each dNTP), 3 μl of 50 mM stock of $MgCl_2$, 5 μl of the forward and reverse primers (100 pmole each), 48.5 μl of water, and 0.5 μl (2.5 U of Taq DNA polymerase. The forward (CadF-F2B) and reverse (CadF-R1B) primers were selected after sequencing the cadF genes from *C. jejuni* F38011 and M129, and one *C. coli* isolate, M275. The CadF-F2B primer (5'-TTG AAG GTA ATT TAG ATA TG-3') (SEQ ID NO: 11) corresponds to nucleotides 101–120 and the CadF-R1B primer (5'-CTA ATA CCT AAA GTT GAA AC-3') (SEQ ID NO: 12 ) to nucleotide 478–497, with a mismatch at nucleotide 489, of the cadF gene from *C. coli* M275. Samples amplified with this primer pair were subjected to 30 cycles of PCR. Each cycle consisted of a denaturing step (1 min, 94° C.), primer annealing (1 min, 45° C.), and chain extension (72° C., 3 min). PCR amplification products (15 μl) were resolved in 1.5% agarose gels and visualized by staining with ethidium bromide. A sample yielding a band of approximately 400 bp was assessed as a positive.

Indirect Immunofluorescence Assays. *C. jejuni* were harvested from MH/blood agar plates in PBS, pelleted by centrifugation, and suspended to approximately $1\times10^8$ bacteria per ml in PBS. Also prepared was a suspension of erythrocytes, which contained approximately 1×107 cells per ml, in PBS. Equal volumes of the bacterial and cells suspensions were mixed and 20 μl of the mixture was allowed to air dry on a glass slides. The slides were immersed in methanol for 5 min, which often exposes epitopes otherwise inaccessible to antibody reactions, rinsed five times in PBS, and incubated in a humidified petri dish at 37° C. for 1 hr with a 1:50 dilution in PBS/Tween of the rabbit anti-*C. jejuni* 37 kDa serum described in Example 1. The slides were then immersed five times, 1 min each rinse, in PBS and incubated in a humidified petri dish at 37° C. for 1 hr with a 1:100 dilution of an affinity purified FITC-labeled goat anti-rabbit IgG (H+L chain) antibody in PBS. Following incubation, the slides were again immersed five times in PBS. A drop of PBS-glycerol (1:1) was then placed on the surface of each slide and a coverslip added. Samples were examined using a Nikon inverted microscope equipped with a krypton-argon laser (Bio-Rad). Images were captured using the Bio-Rad 1024 laser scanning confocal microscopy imaging system and processed using Adobe Photoshop 4.0 (Adobe Systems, Inc., Mountain View, Calif.).

Other Analytical Methods. Based on the sequence of the cadF gene from *C. coli* M275 (previously *C. jejuni* M275), the cadF genes from *C. jejuni* F3801 1 and M129 were PCR amplified using the CadF-F38 forward primer (5-'ATG AAA AAG TTA TTA CTA TGT TTA GG-3') (SEQ ID NO: 13) and CadF-R20 reverse primer (5'-AGG ATA AAT TTA GCA TCC-3') (SEQ ID NO: 14). DNA sequencing was performed using a double-stranded DNA cycle sequencing kit according to the supplier's instructions (Life Technologies Inc.). Sequencing primers were synthesized by Ransom Hill Bioscience, Inc. (Ramona, Calif.) and Life Technologies Inc., Gaithersburg, Md.). Samples were heated to 95° C. for 5 min prior to electrophoresis in 8% polyacrylamide/8M urea sequencing gels in TBE (0.089 M Tris base, 0.089 M boric acid, 0.002 M EDTA, pH 8.0). After electrophoresis, the gels were transferred to 3MM paper (Whatman), dried, and analyzed by autoradiography.

Results

Characterization of Campylobacter Isolates

Bacteria used in these studies included 39 isolates of *C. jejuni*, six isolates of *C. coli*, and several non-Campylobacter species (Table 4). To ensure that these isolates represented a diverse group of *C. jejuni* and *C. coli*, prior to PCR analysis the isolates were subjected to biotyping, serotyping, and pulsed-field gel electrophoresis (PFGE) of DNA digested with restriction endonucleases. The biotyping scheme used was that devised by Lior (1984) and allows for the differentiation of *C. jejuni* into four biotypes and *C. coli* isolates into two biotypes based on hydrogen sulphite production and their ability to hydrolyze DNA The biotype results are given in Table 4. Of the 39 *C. jejuni* isolates tested, 22 (56.4%) belonged to biotype I (H2S−, DNase−), 15 (38.5%) to biotype II (H2S−, DNase+), and two (5.1%) to biotype m (H2S+, DNase−). No *C. jejuni* belonging to biotype IV (H2S+, DNase+) were identified among these isolates. These results are consistent with the biotyping results obtained by Lior (1984) who found that a majority of *C. jejuni* clinical isolates belong to biotype I or II. Also of note in his study was that only 4.0% and 2.7% of the 1,195 *C. jejuni* isolated from humans were found, respectively, to be biotype III or biotype IV. Of the five *C. coli* isolates biotyped in the present study, four were identified as a biotype I (H2S−, DNase−) and one as a biotype II (H2S−, DNase+).

The Campylobacter isolates of Table 4 were also subjected to serotyping using the slide agglutination test which employs viable bacteria (Lior et al., 1982), and the results are included in Table 4. This serotyping scheme is based on heat-labile antigens with a total of 130 antisera. Sixteen different serotypes were observed among the 39 *C. jejuni* isolates tested. Thus, seven of the nine common serotypes (serotypes 1, 2, 3, 6, 7, 9, 11, 16, 17, and 36) in the U.S. were represented among the collection of *C. jejuni* isolates used in this study. The most commonly identified *C. jejuni* serotype was type 36, which occurred six times, and which has been noted previously to be a common serotype in the U.S. (Patton and Wachsmuth, 1992). Seven isolates were found to be untypable with these antisera. These test results indicated a considerable diversity among this group of isolates.

PFGE was performed as described above to characterize the genomic diversity in the *C. jejuni* isolates of Table 4. Initially, the isolates were analyzed by PFGE following digestion of chromosomal DNAs with the restriction enzyme Sal I. PFGE of Sal I-restricted *C. jejuni* chromosomal DNA yielded five or six fragments ranging in size from 38.5 to 1125 kb. By determining the size of the genomic DNA fragments obtained after digestion with the Sal I restriction enzyme, the size of *C. jejuni* genome was estimated to range between 1.8 to 1.95 Mb, depending on the particular isolate analyzed. Based on the relative PFGE pattern following Sal I digestion, the isolates were subdivided into one of eight groups. Isolates within a group exhibited the same sizes and numbers of DNA fragments after PFGE analysis.

Isolates that yielded PFGE patterns that differed by the sizes of one or two bands upon Sal I digestion were then analyzed by PFGE following digestion with Kpn I. Consistent with previous studies (Gibson et al., 1997), digestion of the *C. jejuni* DNA with the restriction enzyme Kpn I these *C. jenuni* CadF genes, it is likely that the 5' and 3' ends of these *C. jenuni* cadF genes are similar or identical in sequence to the corresponding regions cadF-M275.

As summarized in Table 5, the comparison of the nucleotide sequences of the three cadF genes as shown in revealed that within the compared regions the *C. coli* cadF gene shares 87.4% and 84.7% identity with the cadF genes from *C. jejuni* F38011 and M129, respectively, while the cadF genes from *C. jejuni* F38011 and M129 share a 98.6% identity.

TABLE 5

Comparison of the CadF Nucleotide and Deduced Amino Acid Sequence from *Campytobacter coli* M275 with the CadF Gene and Protein from Two *C. jejuni* Isolates and the Gene Encoding the Outer Membrane Protein F (OmpF) from Pseudomonas Species

| Organism/Gene | Nucleotide Sequence Data | | | Predicted Polypeptide Data | | |
|---|---|---|---|---|---|---|
| | Number of Nucleotides | % G + C | % Identity | Number of Amino Acids | Molecular Mass (kDa) | % Similarity (% Identity) |
| *C. coli* M275 CadF | 981 | 34.6 | 100 | 326 | 36.7 | 100 (100) |
| *C. jejuni* F38011 CadF | 861* | 31.8 | 87.4 | 287* | — | 89.2 (83.3) |
| *C. jejuni* M129 CadF | 861* | 32.2 | 84.7 | 287* | — | 88.9 (83.3) |
| *P. aeruginosa* oprF | 1053 | 59.8 | 41.6 | 350 | 37.6 | 52.3 (28.5) |
| *P. fluorescens* oprF | 981 | 56.8 | 39.7 | 326 | 34.5 | 51.4 (28.4) |

*Computer analyses performed using a partial nucleotide sequence.

commonly yielded fragments ranging from 48.5 to 365 kb. None of the *C. jejuni* isolates showing a similar pattern by Sal I digestion yielded an identical PFGE pattern upon Kpn I digestion, suggesting that each of these isolates was unique. It is noteworthy that even though three of the serotype 36 *C. jejuni* strains were isolated from the same geographical region over a relatively short period of time, none of these three isolates were identical to one another as judged by their PFGE banding profile.

Extracts of the strains listed in Table 4 were further subjected to immunoblotting with a rabbit anti-CadF antiserum. The CadF protein was found to be conserved in size and antigenicity among every one of these *C. jejuni* and *C. coli* strains (n=46) tested (results shown in Table 6). Moreover, the antibody-based assay was specific, as no cross-reactivity was observed when the rabbit anti-37 kDa serum was used to screen whole-cell extracts of *C. hyointestinalis* or several non-Campylobacter strains.

Isolation and Analysis of cadF Genes from *C. jejuni* M129 and F38011. The CadF-F38 (SEQ ID NO: 13) and CadF-R20 (SEQ ID NO: 14) primers flanking the 5' and 3' ends of the cadF gene from *C. coli* M275 were used to amplify the cadF genes from *C. jejuni* isolates F38011 and M129. The resulting products were sequenced, and the three sequences were aligned. Efforts were not made to determine nucleotide sequences at the extreme 5' and 3' termini of the *C. jejuni* M129 and F38011 cadF genes, thus the sequences for these genes are not complete. However, given that the M275-derived primers CadF-F38 and CadF-R20 served to amplify Several pairs of PCR primers were designed to attempt to amplify at least a portion of the cadF gene from all of the *C. jejuni* isolates. Following PCR amplification with these primers, the products were separated in 1.5% agarose gels and visualized by staining with ethidium bromide. Preliminary analyses revealed that one primer pair, designated CadF-F2B (forward) (SEQ ID NO: 11) and CadF-R1B (reverse) (SEQ ID NO: 12), amplified a product of approximately 400 bp from each of the *C. jejuni* isolates tested. These two primers correspond to nucleotides 101–120 and 478–497 of the *C. coli* M275 cadF gene, as indicated in In further analyses, it was determined that a 400 bp fragment of DNA could be PCR-amplified from 38 of the 40 *C. jejuni* isolates and 5 of the 6 *C. coli* isolates listed in Table 6 by PCR using the cadF-F2B and cadF-R1B primers. The 400 bp band was not detected in *C. hyointestinalis, H. pylon, P. aeruginosa, S. flexneri, S. typhimurium*, and *E. coli* isolates using this pair of PCR primers (see Table 6), thus the specificity of the assay was determined to be 100%. These data suggested that the cadF gene is fairly well conserved among Campylobacter isolates and that a PCR assay using the cadF-F2B and cadF-R1B primers is capable of the specific detection of most variants of *C. coli* or *C. jejuni* in food or water samples, or in patient samples. The isolation of additional cadF genes and comparison of their sequences with those in SEQ ID NO: 1, SEQ ID NO: 5 and SEQ ID NO: 7 will provide the basis for designing additional PCR probes capable of detecting cadF genes. Use of these additional PCR primers, alone or in conduction with CadF-F2B and CadF-R1B, will provide sensitive assays capable of detecting all variants of the cadF gene.

TABLE 6

PCR Amplification and Immunoblot Detection of CadF

| Strain | PCR Product F2B/R1B | F2B/R1C or F2B/R1E | Immunoblot Detection |
|---|---|---|---|
| *C. jejuni* Isolates | | | |
| 33560 | + | | + |
| F38011 | + | | + |
| M129 | + | | + |
| H70100 | + | | + |
| M95 | + | | + |
| M98 | + | | + |
| M125 | + | | + |
| M128 | + | | + |
| M369 | + | | + |
| M521 | + | | + |
| M48789 | − | | + |
| W52400 | + | | + |
| X34578 | + | | + |
| St. Joseph | + | | + |
| St. M 3143 | + | | + |
| St.M F1474 | + | | + |
| St. M T6644 | + | | + |
| St.M W726 | + | | + |
| UMC T1393 | + | | + |
| T8531 | + | | + |
| TGH3611 | + | | + |
| KLC 100 | − | | + |
| KLC 101 | + | | + |
| KLC 102 | + | | + |
| KLC 106 | + | | + |
| KLC 108 | + | | + |
| KLC 109 | + | | + |
| KLC110 | + | | + |
| KLC111 | + | | + |
| KLC112 | + | | + |
| KLC114 | + | | + |
| E96-1009 | + | | + |
| E97-2653 | + | | + |
| E97-2796 | + | | + |
| E97-2805 | + | | + |
| E97-2845 | + | | + |
| E97-95412 | + | | + |
| 78-27 | + | | + |
| 81116 | + | | + |
| 81176 | + | | + |
| *C. coli* Isolates | | | |
| M275 | + | + | + |
| T1138 | − | − | + |
| T1631 | + | + | + |
| 2144 | + | + | + |
| T2234 | + | + | + |
| INN-18383 | + | + | + |
| Other Isolates | | | |
| *Campylobacter hyointestinalis* | − | | − |
| *Helicobacter pylori* | − | | − |
| *Pseudomonas aeruginosa* | − | | − |
| *Shigella flexneri* | − | | − |
| *Salmonella typhimurium* 85-102840 | − | | − |
| *Escherichia coli* H30 | − | | − |

Further inspection of the cadF genes from *C. coli* M275 and the two *C. jejuni* isolates F38011 and M129 (SEQ ID NO: 13) SEQ ID NO: 1, SEQ ID NO: 5 and SEQ ID NO: 7, revealed several sites containing stretches of bases that appeared to be unique to the *C. coli* cadF gene. Several primers were selected from these stretches of sequence, and used in combination with the cadF-F2B primer to attempt to specifically amplify the cadF gene from only *C. coli* isolates. An 0.4–0.5 kb portion of the cadF gene was successfully amplified by PCR from five of the six *C. coli* isolates, and none of the *C. jejuni* isolates, using the cadF-F2B and cadF-R1C (5'CTTCTTTTACTTGTTCGGCT3') (SEQ ID NO: 16) primers and cadF-F2B and cadF-R1E (5'CATTGTGATTGTGTAGGTAC3') (SEQ ID NO: 18) primers. These data indicate that *C. coli* and *C. jejuni* isolates can be distinguished using a PCR-based assay that exploits the differences in the nucleotide sequences in the cadF genes from *C. coli* and *C. jejuni*.

Sensitivity of the PCR Assay. The sensitivity of the PCR assay using the cadF-F2B and cadF-R1B primers was assessed by preparing ten-fold serial dilutions (106 to 100) of *C. jejuni* F38011 in Eagle's Minimal Essential Medium. The viable number of *C. jejuni* in each sample was quantitated by plating the bacterial suspensions on MH/blood agar plates. Results indicated that the 400 bp product could be visualized using DNA from as few as 100 bacteria to provide the PCR template.

Another goal of this study was to further confirm that the CadF protein could be detected in most or all *C. coli* and *C. jejuni* isolates using a rabbit antiserum raised against the gel-elected 37 kDa CadF protein. For these analyses, bacterial whole-cell extracts from the bacteria listed in Table 6 (25 μg per lane) were separated in 12.5% SDS-PAGE gels and proteins transferred to PVDF membranes. The membranes were then reacted with a 1:250 dilution of the rabbit anti-37 kDa serum prepared as described in Example 1. As indicated in Table 6, a band of approximately 37 kDa, corresponding to the CadF protein, was detected in every one *C. jejuni* and *C. coli* isolate tested. In contrast, a reactive band was not visualized in the whole-cell extracts of any of the control bacteria, which were *C. hyointestinalis, H. pylori, P. aeruginosa, S. flexneri, S. typhimurium,* or *E. coli*. These findings indicate that the CadF protein is specific to *C. coli* and *C. jejuni*, and that it is highly conserved in size and immunogenicity among isolates of these two species of Campylobacter. Antiserum against the 37 kDa CadF protein thus is useful in assays to specifically detect *C. jejuni* and *C. coli* organisms in samples of food, water, soil, stool, etc.

Southern Blot Analysis of the cadF Gene.

In other experiments, Southern blots were performed using as a hybridization probe a nick-translated cadF-F28/cadF-RIB PCR product from Cj F38011. When hybridized with DNA from a large number of *C. coli* and *C. jejuni* isolates, a positive hybridization result was obtained for all isolates tested, thus again confirming the presence of the cadF gene in these two species of Campylobacter, and indicating that hybridization and PCR assays provide a useful means of analyzing samples to detect the presence of *C. coli* or *C. jejuni*. These hybridizations were conducted under moderately stringent conditions in which the hybridization buffer contained 50% formamide and 1 M NaCl, and in which hybridization was conducted at 37° C. Filters were washed after the hybridization step in 2×SSC at room temperature, then in 2×SSC at 37° C. to 40° C. (1×SSC=0.15 M NaCl/0.015 M sodium citrate).

Detection of Campylobacter Organisms by Indirect Immunofluorescence Microscopy. To determine whether Campylobacter organisms could be detected using an indirect immunofluorescence microscopy assay, two *C. jejuni* isolates (M98 and M129) and two non-Campylobacter isolates (*Salmonella typhimurium* 85–102840 and *E. coli* H30) were reacted with a 1:50 dilution of the above-described rabbit anti-37 kDa serum followed by incubation with a 1:100 dilution of an affinity purified FITC-labeled goat anti-rabbit IgG (H+L chain) antibody in PBS as described above. Standard immunofluorescence staining demonstrated that the rabbit anti-37 kDa serum bound efficiently to both isolates *C. jejuni* but not to the *S. typhimurium* or *E. coli*, thus indicating that antisera against this protein are useful in assays and test kits that employ a direct or indirect fluorescence antibody test, or for an ELISA assay using CadF-coated plates, to determine whether an individual has been infected with *C. jejuni* or *C. coli*. In this regard, it is explained above (Example 1) that antibodies present in convalescent antiserum from *C. jejuni*-infected individuals was determined to recognize the 37 kDa protein. Moreover, an ELISA assay for detecting CadF may be helpful in documenting GBS individuals who have previously been infected with *C. jejuni* or *C. coli*.

While the preferred embodiment of the invention has been illustrated and described, it will be appreciated that various changes can be made therein without departing from the spirit and scope of the invention.

REFERENCES

Baloda, S. B., Faris, A., Froman, G., and Waldstrom, T. (1985). Fibronectin binding to Salmonella strains. *FEMS Microbiol. Lett.* 28: 1–5.

Bellido, F., Martin, N. L., Siehnel, R. J., and Hancock, R. E. W. (1992). Reevaluation, using intact cells, of the exclusion limit and role of porin OprF in *Pseudomonas aeruginosa* outer membrane permeability. *J. Bacteriol.* 174: 5196–5203.

Bolla, J. -M., Loret, E., Zalewski, M., and Pages, J. -M. (1995). Conformational analysis of the *Campylobacter jejuni* porin. *J. Bacteriol.* 177: 4266–4271.

Chang, N., and D. E. Taylor (1990). Use of Pulsed-field agarose gel electrophoresis to size genomes of Campylobacter species to construct a Sal I map of *Campylobacter jejuni* UA580. *J. Bacteriol.* 172: 5211–5217.

Chen, R., and Henning, U. (1987). Nucleotide sequence of the gene for the peptidoglycan-associated lipoprotein of *Escherichia coli* K12. *Eur. J. Biochem.* 163: 73–77.

Consumer Reports, vol. 63, p. 12–18, 1998. Chicken: What you don't know can hurt you.

Dawson, J. R., and Ellen, R. P. (1990). Tip-oriented adherence of *Treponema denticola* to fibronectin. *Infect. Immun.* 58: 3924–28.

De Melo, M. A., and Pechere, J. -C. (1990). Identification of *Campylobacter jejuni* surface proteins that bind to eukaryotic cells in vitro. *Infect. Immun.* 58: 1749–1756.

De Mot, R., Proost, P., Van Damme, J., and Vanderleyden, J. (1992). Homology of the root adhesin of *Pseudomonas fluorescens* OE28.3 with porin F of *P. aeruginosa* and *P. syringae*. *Mol. Gen. Genet.* 231: 489–493.

De Mot, R., Schoofs, G., Roelandt, A., Declerck, P., Proost, P., Van Damme, J., and Vanderleyden, J. (1994). Molecular characterization of the major outer-membrane protein OprF from plant colonizing *Pseudomonas fluorescens*. *Microbio.* 140: 1377–1387.

De Mot, R., and Vanderleyen, J. (1991). Purification of a root-adhesive outer membrane protein of root-colonizing *Pseudomonas fluorescens*. *FEMS Microbiol Lett.* 81: 323–328.

Deich, R. A., Metcalf, B. J., Finn, C. W., Farley, J. E., and Green, B. A. (1988). Cloning of genes encoding a 15,000-Dalton peptidoglycan-associated outer membrane lipoprotein and an antigenically related 15,000-Dalton protein from *Haemophilus influenzae*. *J. Bacteriol.* 170: 489–498.

Engleberg, N. C., Howe, D. C., Rogers, J. E., Arroyo, J., and Eisenstein, B. I. (1991). Characterization of a *Legionella pneumophila* gene encoding a lipoprotein antigen. *Mol. Microbiol.* 5: 2021–2029.

Fauchere, J. L., Rosenau, A., Veron, M., Moyen, E. N., Richard, S., and Pfister, A. (1986). Association with HeLa cells of *Campylobacter jejuni* and *Campylobacter coli* isolated from human feces. *Infect. Immun.* 54: 283–287.

Fraker, P. J., and Speck, J. C. Jr. (1978). Protein and cell membrane iodinations with a sparingly soluble chloroamide, 1,3,4,6-tetrachloro-3a,6a-diphenyl-glycouril. *Biochem. Biophys. Res. Commun.* 80: 849–857.

Froman, G., Switalski, L. M., Faris, A., Wadstrom, T., and Hook, M. (1984). Binding of *Escherichia coli* to fibronectin. *J. Biol. Chem.* 259: 14899–14905.

Garvis, S. G., Puzon, G. J., and Konkel, M. E. (1996). Molecular characterization of a *Campylobacter jejuni* 29-Kilodalton periplasmic binding protein. *Infect. Immun.* 64: 3537–3543.

Gibson, J., E. Lorenz, and R. J. Owen. (1997). Lineages within *Campylobacter jejuni* defined by numerical analysis of pulsed-field gel electrophoretic DNA profiles. *J. Med. Microbiol.* 46: 157–163.

Hwang, M. N., and A. M. Ederer (1975). Rapid hippurate hydrolysis method for presumptive identification of group B streptococci. *J. Clin. Microbiol.* 1: 114–115.

Isberg, R. R., and Van Nhieu, G. T. (1994). Two mammalian cell internalization strategies used by pathogenic bacteria. *Annu. Rev. Genet.* 28: 395–422.

Keski-Oja, J., Hautanen, A., and Julkunen, I. (1987). Fibronectin and viral pathogenesis. *Rev. Infect. Dis.* 9: S404–411.

Koebnik, R. (1995). Proposal for a peptidoglycan-associating alpha-helical motif in the C-terminal regions of some bacterial cell-surface proteins. *Mol. Microbiol.* 16: 1269–1270.

Konkel, M. E., and Cieplak, W., Jr. (1992). Altered synthetic response of *Campylobacter jejuni* to co-cultivation with human epithelial cells is associated with enhanced internalization. *Infect. Immun.* 60: 4945–4949.

Konkel, M. E., Corwin, M. D., Joens, L. A., and Cieplak, W., Jr. (1992). Factors that influence the interaction of *Campylobacter jejuni* with cultured epithelial cells. *J. Med. Microbiol.* 37: 30–37.

Konkel, M. E., Hayes, S. F., Joens, L. A., and Cieplak, W., Jr. (1993a). Characteristics of the internalization and intracellular survival of *Campylobacter jejuni* in human epithelial cell cultures. *Microbial. Pathog.* 13: 357–370.

Konkel, M. E., and Joens, L. A. (1989). Adhesion to and invasion of HEp-2 cells by Campylobacter spp. *Infect. Immun.* 57: 2984–2990.

Konkel, M. E., Mead, D. J., and Cieplak, W., Jr. (1996). Cloning, sequencing, and expression of a gene from *Campylobacter jejuni* encoding a protein (Omp18) with similarity to peptidoglycan-associated lipoproteins. *Infect. Immun.* 64: 1850–1853.

Konkel, M. E., Mead, D. J., and Cieplak, W., Jr. (1993b). Kinetic and antigenic characterization of altered protein synthesis by *Campylobacter jejuni* during cultivation with human epithelial cells. *J. Infect. Dis.* 168: 948–954.

Konkel, M. E., S. G. Garvis, S. L. Tipton, D. E. Anderson, Jr., and W. Cieplak Jr. (1997). Identification and molecular cloning of a gene encoding a fibronectin-binding protein (CadF) from *Campylobacter jejuni. Mol. Microbiol.* 24: 953–963.

Kuroki, S., Haruta, T., Yoshioka, M., Kobayashi, Y., Nukina, M., and Nakanishi, H. (1991). Guillain-Barre syndrome associated with Campylobacter infection. *Pediatr. Infect. Dis. J.* 10: 149–151.

Kuusela, P. (1978). Fibronectin binds to *Staphylococcus aureus. Nature* (Lond) 276: 718–20.

Kuusela, P., Moran, A. P., Vartio, T., and Kosunen, T. U. (1989). Interaction of *Campylobacter jejuni* with extracellular matrix components. *Biochem. Biophys. Acta.* 993: 297–300.

Laemmli, U. K. (1970). Cleavage of structural proteins during the assembly of the head of bacteriophage T4. *Nature* 227: 680–685.

Lazzaroni, J. -C., and Portalier, R. (1992). The excC gene of *Escherichia coli* K-12 required for cell envelope integrity encodes the peptidoglycan-associated lipoprotein (PAL). *Mol. Microbiol.* 6: 735–742.

Lior, H., and A. Patel (1987). Improved toluidine blue-DNA agar for detection of DNA hydrolysis by campylobacters. *J. Clin. Microbiol.* 25: 2030–2031.

Lior, H., D. L. Woodward, J. A. Edgar, L. J. Laroche, and P. Gill (1982). Serotyping of *Campylobacter jejuni* by slide agglutination based on heat-labile antigenic factors. *J. Clin. Microbiol.* 15: 761–768.

Logan, S. M., and Trust, T. J. (1982). Outer membrane characteristics of *Campylobacter jejuni. Infect. Immun.* 38: 898–906.

Ludwig, B., Schmid, A., Marre, R., and Hacker, J. (1991). Cloning, genetic analysis, and nucleotide sequence of a determinant coding for a 19-kilodalton peptidoglycan-associated protein (Ppl) of *Legionella pneumophila. Infect Immun.* 59: 2515–21.

Marconi, R. T., Samuels, D. S., and Garon, C. F. (1993). Transcriptional analyses and mapping of the ospC gene in Lyme disease spirochetes. *J. Bacteriol.* 175: 926–932.

McSweegan, E., and Walker, R. I. (1986). Identification and characterization of two *Campylobacter jejuni* adhesins for cellular and mucous substrates. *Infect. Immun.* 53: 141–148.

Moser, I., and Schroder, W. (1995). Binding of outer membrane preparations of *Campylobacter jejuni* to INT407 cell membranes and extracellular matrix proteins. *Med. Microbio. Immunol.* 184: 147–153.

Myhre, E. B., and Kuusela, P. (1983). Binding of human fibronectin to group A, C, and G streptococci. *Infect. Immun.* 40: 29–34.

Nelson, M. B., Apicella, M. A., Murphy, T. F., Vankeulen, H., Spotila, L. D., and Rekosh, D. (1988). Cloning and sequencing of *Haemophilus influenzae* outer membrane protein P6. *Infect. Immun.* 56: 128–134.

Nikaido, H., Nikaido, K., and Harayama, S. (1991). Identification and characterization of porins in *Pseudomonas aeruginosa. J. Biol. Chem.* 266: 770–779.

Patton, C. M., and I. K. Wachsmuth (1992). Typing schemes: Are current methods useful?, p. 110–128. In I. Nachamkin and M. J. Blaser and L. S. Tompkins (ed.), *Campylobacter jejuni*: Current status and future trends. American Society for Microbiology, Washington, D.C.

Pei, Z., and Blaser, M. J. (1993). PEB1, the major cell-binding factor of *Campylobacter jejuni*, is a homolog of the binding component in gram-negative nutrient transport systems. *J. Biol. Chem.* 268: 18717–18725.

Pei, Z., Ellison, R. T., III, and Blaser, M. J. (1991). Identification, purification, and characterization of major antigenic proteins of *Campylobacter jejuni. J. Biol. Chem.* 266: 16363–16369.

Quaroni, A., Isselbacher, K. J., and Ruoslahti, E. (1978). Fibronectin synthesis by epithelial crypt cells of rat small intestine. *Proc. Natl. Acad. Sci.* USA 75: 5548–5552.

Ropper, A. H. (1992). The Guillain-Barre syndrome. *N. Engl. J. Med.* 326: 1130–1136.

Skirrow, M. B., and Blaser, M. J. (1992). Clinical and epidemiologic considerations. In *Campylobacter jejuni. Current Status and Future Trends*Nachamkin, I., Blaser, M. J., Tompkins, L. S. (eds.). American Society for Microbiology, pp. 3–8.

Skirrow, M. B., and J. Benjamin (1980). Differentiation of enteropathogenic campylobacter. *J. Clin. Pathol.* 33: 1122.

Smith, P. K., Krohn, R. I., Hermanson, G. T., Mallia, A. K., Gartner, F. H., Provenzano, M. D., Fujimoto, E. K., Goeke, N. M., Olson, B. J., and Klenk, B. C. (1985). Measurement of protein using bicinchoninic acid. *Anal. Biochem.* 150: 76–85.

Thomas, D. D., Baseman, J. B., and Alderete, J. F. (1985). Fibronectin mediates Treponema pallidum cytadherence through recognition of fibronectin cell-binding domain. *J. Ex. Med.* 161: 514–525.

Tibor, A., Weynants, V., Denoel, P., Lichtfouse, B., DeBolle, X., Saman, E., Limet, J. N., and Letesson, J. -J. (1994). Molecular cloning, nucleotide sequence, and occurrence of a 16.5-kilodalton outer membrane protein of *Brucella abortus* with similarity to PAL lipoproteins. *Infect. Immun.* 62: 3633–3639.

Von Heijne, G. (1985). Signal sequences. The limits of variation. *J. Mol. Biol.* 184: 99–105.

Walsh, F. S., M. Cronin, S. Koblar, P. Doherty, J. Winer, A. Leon, and R. A. Hughes (1991). Association between glycoconjugate antibodies and Campylobacter infection in patients with Guillain-Barre syndrome. *J. Neuroimmunol.* 34: 43–51.

Wyler, D. J. (1987). Fibronectin and parasitic diseases. *Rev. Infect. Dis.* 9: S391–S399.

Yuki, N., Taki, T., Inagaki, F., Kasama, T., Takahashi, M., Saito, K., Handa, S., and Miyatake, T. (1993). A bacterium lipopolysaccharide that elicits Guillain-Barre syndrome has a GM1 ganglioside-like structure. *J. Exp. Med*. 178: 1771–1775.

Yuki, N., T. Taki, M. Takahashi, K. Saito, T. Tai, T. Miyatake, and S. Handa (1994). Penner's serotype 4 of *Campylobacter jejuni* has a lipopolysaccharide that bears a GM1 ganglioside epitope as well as one that bears a GD1a epitope. *Infect. Immun*. 62: 2101–2103.

The embodiments of the invention in which an exclusive property or privilege is claimed are defined as follows:

1. An isolated polynucleotide that encodes a *Campylobacter jejuni* or *Campylobacter coli* CadF polypeptide and which specifically hybridizes to a nucleic acid molecule selected from the group consisting of the nucleic acid sequences set forth in SEQ ID NO: 1, SEQ ID NO: 5, and SEQ ID NO: 7 or their complements.

2. An isolated polynucleotide according to claim 1, wherein the isolated polynucleotide encodes a CadF polypeptide having the amino acid sequence encoded by a cadF gene selected from the group consisting SEQ ID NO: 2, SEQ ID NO: 6 and SEQ ID NO: 8.

3. An isolated polynucleotide according to claim 2, wherein the CadF polypeptide has the amino acid sequence set forth in SEQ ID NO: 2.

4. An isolated polynucleotide that encodes a polypeptide comprising at least 12 contiguous amino acids of the amino acid sequence set forth in SEQ ID NO: 2.

5. An isolated polynucleotide that encodes a CadF polypeptide and that hybridizes with a pair of PCR primers having the nucleotide sequences set forth in SEQ ID NO: 9 and SEQ ID NO: 10.

6. An isolated polynucleotide according to claim 5, wherein the isolated polynucleotide has a nucleotide sequence selected from the group consisting of the nucleotide sequences set forth in SEQ ID NO: 1, SEQ ID NO: 5 and SEQ ID NO: 7.

7. A recombinant expression vector comprising the isolated nucleic acid molecule of claim 1.

8. Cells transfected or transduced with the recombinant expression vector of claim 7.

9. A nucleic acid probe specific for the detection of *Campylobacter jejuni* or *Campylobacter coli*, comprising an isolated nucleic acid molecule at least 10 nucleotides in length that hybridizes in 2×SSC at 37° C. to 40° C. to a DNA molecule selected from among the group consisting of the nucleotide sequences set forth in SEQ ID NO: 1, SEQ ID NO: 5 and SEQ ID NO: 11 or their complements, but not to genomic DNA of *Campylobacter hyointestinalis*.

10. A pair of PCR primers that specifically amplify a DNA fragment from *Campylobacter jejuni* or *Campylobacter coli*, said primers each comprising an isolated nucleic acid molecule at least 10 nucleotides in length that hybridizes at 10° C. below its melting temperature to a cadF DNA molecule having a nucleotide sequence selected from among the group consisting of the nucleotide sequences set forth in SEQ ID NO: 1, SEQ ID NO: 5 and SEQ ID NO: 11 or their complements, but not to the DNA of *Campylobacter hyointestinalis*.

11. A pair of PCR primers according to claim 10, wherein said primer pair is selected from the group consisting of the following sets of primer pairs:

Set 1: 5'-TTGAAGGTAA TTTAGATATG-3' (forward) [SEQ ID NO: 11]
5'-CTAATACCTA AAGTTGAAAC-3' (reverse) [SEQ ID NO: 12] and Set 2: 5'-ATGAAAAAGT TATTACTATG TTTAGG-3' (forward) [SEQ ID NO: 13]
5'-AGGATAAATT TAGCATCC-3' (reverse) [SEQ ID NO: 14].

12. An assay for determining the presence of *Campylobacter jejuni* or *Campylobacter coli* in a test sample, comprising the steps:

(a) annealing DNA from the test sample with a pair of PCR primers that each hybridize at 10° C. below their respective melting temperatures to DNA from *Campylobacter jejuni* or *Campylobacter coli* but not to DNA from *Campylobacter hyointestinalis*, and that flank a DNA fragment of known size;

(b) conducting a PCR reaction to produce an amplified DNA product;

(c) analyzing the amplified DNA product; and (d) detecting the presence of the amplified DNA product as indicative of the presence of *Campylobacter jejuni* or *Campylobacter coli*.

13. The assay of claim 12, wherein the pair of PCR primers is selected from the primer pairs:

Set 1: 5'-TTGAAGGTAA TTTAGATATG-3' (forward) [SEQ ID NO: 11]
5'-CTAATACCTA AAGTTGAAAC-3' (reverse) [SEQ ID NO: 12] and Set 2: 5'-ATGAAAAAGT TATTACTATG TTTAGG-3' (forward) [SEQ ID NO: 13]
5'-AGGATAAATT TAGCATCC-3' (reverse) [SEQ ID NO: 14].

14. An assay for determining whether a test isolate of Campylobacter is a strain of *Campylobacter coli* comprising the steps:

(a) annealing DNA from the test isolate with a pair of PCR primers selected from the following sets of PCR primers:

Set 1: 5'-TTGAAGGTAA TTTAGATATG-3' (forward) [SEQ ID NO: 11]
5'-CTTCTTTTAC TTGTTCGGCT-3' (reverse) [SEQ ID NO: 12] and
Set 2: 5'-TTGAAGGTAA TTTAGATATG-3' (forward) [SEQ ID NO: 13]
5'-CATTGTGATT GTGTAGGTAC-3' (reverse) [SEQ ID NO: 14];

(b) conducting a PCR reaction to produce an amplified DNA product;

(c) analyzing the amplified DNA product; and (d) determining that the test isolate is a strain of *Campylobacter coli* if a DNA fragment of 0.4–0.5 kb is detected in the analysis of the amplified DNA product.

* * * * *

UNITED STATES PATENT AND TRADEMARK OFFICE
CERTIFICATE OF CORRECTION

PATENT NO. : 6,156,546
DATED : December 5, 2000
INVENTOR(S) : M.E. Konkel et al.

It is certified that error appears in the above-identified patent and that said Letters Patent is hereby corrected as shown below:

Title page,
Item [56], References Cited, "OTHER PUBLICATIONS",
"*Micrbiol.*" should read -- *Microbiol.* --
"75:5548-5552(1978)." should read -- 75:5548-5552 (1978). --

Column 2,
Line 4, "*C. coil*" should read -- *C. coli,* --
Line 14, "Staphlococcus" should read -- Staphylococcus --
Line 22, "*C. coli ,*" should read -- *C. coli,* --

Column 3,
Line 28, "infected-individuals" should read -- infected individuals --
Line 55, after "nucleic acids" delete ","

Column 4,
Line 44, "my multiplying" should read -- by multiplying --

Column 5,
Line 17, "*Vol.* 52," should read -- Vol. 52, --
Line 28, after "residues from" delete "the"
Line 36, "product's" should read -- products'-

Column 6,
Line 30, "Opr" should read -- OprF --
Line 60, "kDa," should read -- kDa. --

Column 7,
Line 15, "F3801 1," should read -- F38011, --
Line 60, "NO: 2" should read -- NO: 1 --

Column 9,
Line 6, "oligonucleotides" should read -- oligonucleotide --

Column 10,
Lines 42-43, delete "and SEQ ID NO: 7" and insert therefor -- or SEQ ID NO: 7, or their complements --

Column 11,
Line 15, delete "that", second occurrence
Line 38, "Np143" should read -- M3143 --

UNITED STATES PATENT AND TRADEMARK OFFICE
CERTIFICATE OF CORRECTION

PATENT NO. : 6,156,546
DATED : December 5, 2000
INVENTOR(S) : M.E. Konkel et al.

It is certified that error appears in the above-identified patent and that said Letters Patent is hereby corrected as shown below:

Column 12,
Line 24, "of$^{125}$I-Fn" should read -- of $^{125}$I-Fn --
Line 53, "meta-periodate" should read -- *meta*-periodate --

Column 14,
Line 4, "etal." should read -- et al. --
Line 7, "Sau3AI or Bgl II" should read -- *Sau*3A I or *Bgl* II --
Lines 28-29, "preformed" should read -- performed --
Line 44, "EcoR" should read -- *Eco*R --
Line 47, "EcoR" should read -- *Eco*R --

Column 15,
Line 61, "meta-periodate" should read -- *meta*-periodate --

Column 16,
Line 13, "meta-periodate" should read -- *meta*-periodate --
Line 45, after "lysates" insert -- of --

Column 17,
Line 45, "lac" should read -- *lac* --

Column 19,
Line 34, "Omp 18" should read -- Omp18 --
Line 40, "Enterobacteriaceae" should read -- *Enterobacteriaceae* --
Line 65, "Pseudomonas species" should read -- *Pseudomonas species* --

Column 20,
Line 2, after "used" delete "us"
Line 28, "*pylon*" should read -- *pylori* --

Column 21,
Line 28, "Pseudomomonas" should read -- Psuedomonas --
Line 51, the phrase "rapid H2S test." should read -- Rapid H2S Test. -- and should begin a new paragraph Column 22,
Line 1, after "through" delete -- the --
Line 6, "*tphimurium*" should read -- *typhimurium* --
Line 14, "manufacturers" should read -- manufacturer's --

UNITED STATES PATENT AND TRADEMARK OFFICE
CERTIFICATE OF CORRECTION

PATENT NO. : 6,156,546
DATED : December 5, 2000
INVENTOR(S) : M.E. Konkel et al.

It is certified that error appears in the above-identified patent and that said Letters Patent is hereby corrected as shown below:

Column 23,
Line 13, "concentration;" should read -- concentration: --
Line 15, after "(2.5 U" insert -- ) --
Line 38, "1x107" should read -- 1x10$^7$ --
Line 39, "cells" should read -- cell --
Line 41, "a glass slides." should read -- glass slides. --
Line 64, "F3801 1" should read -- F38011 --

Column 24,
Line 6, "Inc., Gaithersberg" should read -- Inc. (Gaithersberg --
Line 26, "DNA The" should read -- DNA. The --
Line 29, "biotype m" should read -- biotype III --

Column 26,
Line 1, "*C. jenuni*" should read -- *C. jejuni* --
Line 2, "*C. jenuni*" should read -- *C. jejuni* --
Line 6, "genes as shown in revealed that within" should read -- genes shown revealed that within --
Table 5, Heading, Line 16, "Campytobacter" should read -- Campylobacter --
Line 24, "89.2(83.3)" should read -- 89.2 (83.3) --
Line 47, delete "gene, as indicated in" and insert therefor -- gene. --
Line 52, "*pylon*," should read -- *pylori*, --

Column 27,
Line 25, "St.M" should read -- St. M --
Line 27, "St.M" should read -- St. M --
Lines 64-65, after "M129" delete "(SEQ ID NO: 13)"

Column 28,
Line 17, "(106 to 100)" should read -- (10$^6$ to 10$^0$) --
Line 36, before "*C. jejuni*" delete "one"

Column 29,
Line 12, after "isolates" insert -- of --
Line 33, "Salmonella" should read -- *Salmonella* --
Line 41, "J. -M." should read -- J.-M. -- (both instances)
Line 58, "J. -C." should read -- J.-C. --

Column 30,
Line 3, "*Microbio.*" should read -- *Microbiol.* --
Line 67, "*Microbial.*" should read -- *Microbiol.* --

UNITED STATES PATENT AND TRADEMARK OFFICE
CERTIFICATE OF CORRECTION

PATENT NO.   : 6,156,546
DATED        : December 5, 2000
INVENTOR(S)  : M.E. Konkel et al.

It is certified that error appears in the above-identified patent and that said Letters Patent is hereby corrected as shown below:

Column 31,
Line 35, "J. -C." should read -- J.-C. -- and "excC" should read -- *excC* --
Line 66, "extraceliular" should read -- extracellular --
Line 68, "*Microbio.*" should read -- *Microbiol.* --

Column 32,
Line 29, "USA" should read -- *USA* --
Line 35, "*Trends*Nachamkin," should read -- *Trends* Nachamkin, --
Line 50, "*Ex.*" should read -- *Exp.* --
Line 52, "J. -J." should read -- J.-J. --
Line 62, "glycocongugate" should read -- glycoconjugate --

Column 53,
Line 24, "specidically" should read -- specifically --
Line 31, after "consisting" insert -- of --

Signed and Sealed this

Twenty-ninth Day of January, 2002

*Attest:*

*Attesting Officer*

JAMES E. ROGAN
*Director of the United States Patent and Trademark Office*